US012428687B2

(12) United States Patent
Dong et al.

(10) Patent No.: US 12,428,687 B2
(45) Date of Patent: Sep. 30, 2025

(54) RPA-PAND BASED ENTEROVIRUS TYPING DETECTION KIT AND DETECTION METHOD

(71) Applicant: Hubei University, Wuhan (CN)

(72) Inventors: Yanming Dong, Wuhan (CN); Lixin Ma, Wuhan (CN); Xuan Yang, Wuhan (CN); Yuan Wang, Wuhan (CN); Yibin Cheng, Wuhan (CN); Junbo Cao, Wuhan (CN)

(73) Assignee: Hubei University, Wuhan (CN)

( * ) Notice: Subject to any disclaimer, the term of this patent is extended or adjusted under 35 U.S.C. 154(b) by 0 days.

(21) Appl. No.: 18/961,447

(22) Filed: Nov. 27, 2024

(65) Prior Publication Data

US 2025/0092473 A1 Mar. 20, 2025

(30) Foreign Application Priority Data

Apr. 28, 2024 (CN) ......................... 202410521879.8

(51) Int. Cl.
*C12Q 1/70* (2006.01)

(52) U.S. Cl.
CPC ....... *C12Q 1/701* (2013.01); *C12Q 2600/158* (2013.01)

(58) Field of Classification Search
CPC .................................................... C12Q 1/6844
See application file for complete search history.

(56) References Cited

U.S. PATENT DOCUMENTS

2009/0070898 A1* 3/2009 Allen ................. C12N 15/8238 435/320.1
2011/0070586 A1* 3/2011 Slezak ................... C12Q 1/701 435/6.14

(Continued)

FOREIGN PATENT DOCUMENTS

WO WO-2017040316 A1 * 3/2017 ............ C07H 21/04

OTHER PUBLICATIONS

Akarapipad et al. Emerging Multiplex Nucleic Acid Diagnostic Tests for Combating COVID-19. Biosensors (Basel). Nov. 7, 2022;12(11):978. doi: 10.3390/bios12110978. PMID: 36354487; PMCID: PMC9688249 (Year: 2022).*

(Continued)

*Primary Examiner* — Aaron A Priest
*Assistant Examiner* — Tian Nmn Yu
(74) *Attorney, Agent, or Firm* — Hemisphere Law, PLLC; Zhigang Ma

(57) ABSTRACT

Provided are a recombinase polymerase amplification (RPA)-PAND based enterovirus virus typing detection kit and a rapid sensitive detection method, where the detection kit includes a PfAgo protein three gDNAs(g1/g2/g3), MB and its corresponding gDNA(gMB) combination for specifically detection of enteroviruses EV71, CVA6, CVA10, CVA16 and the universal enterovirus (EVU). RPA-HFMD-PAND rapid nucleic acid detection methods for typing detection of common enterovirus type A pathogens EV71, CVA6, CVA10, CVA16 and enterovirus universal EVU are successfully established based on PfAgo protein mediated target detection in combination with an RPA technology. The method has the advantages of high sensitivity, high specificity, low cost, relatively low position targeting restriction, simple reaction system and no aerosol pollution, and can conduct multi-channel nucleic acid detection. The present (Continued)

disclosure provides a new reagent and approach for clinic diagnosis and epidemiology monitoring of a hand-foot-mouth disease (HFMD).

6 Claims, 30 Drawing Sheets

Specification includes a Sequence Listing.

(56) References Cited

U.S. PATENT DOCUMENTS

| | | | | |
|---|---|---|---|---|
| 2012/0282593 | A1 | 11/2012 | McCullers et al. | |
| 2013/0267429 | A1* | 10/2013 | Gardner | C12Q 1/6876 506/8 |
| 2018/0340215 | A1* | 11/2018 | Metsky | C12Q 1/6816 |
| 2021/0164024 | A1 | 6/2021 | Feng et al. | |
| 2023/0184763 | A1 | 6/2023 | Lee | |

OTHER PUBLICATIONS

CNIPA, Notification to grant patent right for Chinese application CN202410521879.8, Sep. 11, 2024.

* cited by examiner

CVA16

SEQUENCE LISTING

```
Sequence total quantity: 123
SEQ ID NO: 1            moltype = DNA  length = 16
FEATURE                 Location/Qualifiers
source                  1..16
                        mol_type = other DNA
                        note = enterovirus universal EVU guide DNA
                        organism = synthetic construct
SEQUENCE: 1
cacggacacc caaagt                                              16

SEQ ID NO: 2            moltype = DNA  length = 16
FEATURE                 Location/Qualifiers
source                  1..16
                        mol_type = other DNA
                        note = enterovirus universal EVU molecular beacon
                        organism = synthetic construct
SEQUENCE: 2
actttgggtg tccgtg                                              16

SEQ ID NO: 3            moltype = DNA  length = 16
FEATURE                 Location/Qualifiers
source                  1..16
                        mol_type = other DNA
                        note = enterovirus universal EVU guide DNA
                        organism = synthetic construct
SEQUENCE: 3
ggaaccgact actttg                                              16

SEQ ID NO: 4            moltype = DNA  length = 15
FEATURE                 Location/Qualifiers
source                  1..15
                        mol_type = other DNA
                        note = enterovirus universal EVU guide DNA
                        organism = synthetic construct
SEQUENCE: 4
ggtgtccgtg ttcct                                               15

SEQ ID NO: 5            moltype = DNA  length = 16
FEATURE                 Location/Qualifiers
source                  1..16
                        mol_type = other DNA
                        note = enterovirus universal EVU guide DNA
```

-continued

```
                        organism = synthetic construct
SEQUENCE: 5
taaaaggaaa cacgga                                              16

SEQ ID NO: 6            moltype = DNA  length = 16
FEATURE                 Location/Qualifiers
source                  1..16
                        mol_type = other DNA
                        note = enterovirus EV71 guide DNA
                        organism = synthetic construct
SEQUENCE: 6
agatgtgact ggtatc                                              16

SEQ ID NO: 7            moltype = DNA  length = 16
FEATURE                 Location/Qualifiers
source                  1..16
                        mol_type = other DNA
                        note = enterovirus EV71 molecular beacon
                        organism = synthetic construct
SEQUENCE: 7
gataccagtc acatct                                              16

SEQ ID NO: 8            moltype = DNA  length = 16
FEATURE                 Location/Qualifiers
source                  1..16
                        mol_type = other DNA
                        note = enterovirus EV71 guide DNA
                        organism = synthetic construct
SEQUENCE: 8
tacccagcca gatacc                                              16

SEQ ID NO: 9            moltype = DNA  length = 16
FEATURE                 Location/Qualifiers
source                  1..16
                        mol_type = other DNA
                        note = enterovirus EV71 guide DNA
                        organism = synthetic construct
SEQUENCE: 9
agtcacatct catgct                                              16

SEQ ID NO: 10           moltype = DNA  length = 16
FEATURE                 Location/Qualifiers
source                  1..16
                        mol_type = other DNA
                        note = enterovirus EV71 guide DNA
                        organism = synthetic construct
SEQUENCE: 10
tgcgagcatg agatgt                                              16

SEQ ID NO: 11           moltype = DNA  length = 16
FEATURE                 Location/Qualifiers
source                  1..16
                        mol_type = other DNA
                        note = enterovirus CVA6 guide DNA
                        organism = synthetic construct
SEQUENCE: 11
aacgtggacg tttttc                                              16

SEQ ID NO: 12           moltype = DNA  length = 16
FEATURE                 Location/Qualifiers
source                  1..16
                        mol_type = other DNA
                        note = enterovirus CVA6 molecular beacon
                        organism = synthetic construct
SEQUENCE: 12
gaaaaacgtc cacgtt                                              16

SEQ ID NO: 13           moltype = DNA  length = 16
FEATURE                 Location/Qualifiers
source                  1..16
                        mol_type = other DNA
                        note = enterovirus CVA6 guide DNA
                        organism = synthetic construct
SEQUENCE: 13
ctaccaccgg gaaaaa                                              16

SEQ ID NO: 14           moltype = DNA  length = 16
FEATURE                 Location/Qualifiers
source                  1..16
```

-continued

```
                         mol_type = other DNA
                         note = enterovirus CVA6 guide DNA
                         organism = synthetic construct
SEQUENCE: 14
cgtccacgtt cgggtg                                                      16

SEQ ID NO: 15            moltype = DNA  length = 16
FEATURE                  Location/Qualifiers
source                   1..16
                         mol_type = other DNA
                         note = enterovirus CVA6 guide DNA
                         organism = synthetic construct
SEQUENCE: 15
tgtacacccg aacgtg                                                      16

SEQ ID NO: 16            moltype = DNA  length = 16
FEATURE                  Location/Qualifiers
source                   1..16
                         mol_type = other DNA
                         note = enterovirus CVA10 guide DNA
                         organism = synthetic construct
SEQUENCE: 16
ttggcttgcc ttccta                                                      16

SEQ ID NO: 17            moltype = DNA  length = 16
FEATURE                  Location/Qualifiers
source                   1..16
                         mol_type = other DNA
                         note = enterovirus CVA10 molecular beacon
                         organism = synthetic construct
SEQUENCE: 17
taggaaggca agccaa                                                      16

SEQ ID NO: 18            moltype = DNA  length = 16
FEATURE                  Location/Qualifiers
source                   1..16
                         mol_type = other DNA
                         note = enterovirus CVA10 guide DNA
                         organism = synthetic construct
SEQUENCE: 18
gagttgtcag taggaa                                                      16

SEQ ID NO: 19            moltype = DNA  length = 16
FEATURE                  Location/Qualifiers
source                   1..16
                         mol_type = other DNA
                         note = enterovirus CVA10 guide DNA
                         organism = synthetic construct
SEQUENCE: 19
ggcaagccaa ctaaaa                                                      16

SEQ ID NO: 20            moltype = DNA  length = 16
FEATURE                  Location/Qualifiers
source                   1..16
                         mol_type = other DNA
                         note = enterovirus CVA10 guide DNA
                         organism = synthetic construct
SEQUENCE: 20
gtagttttag ttggct                                                      16

SEQ ID NO: 21            moltype = DNA  length = 16
FEATURE                  Location/Qualifiers
source                   1..16
                         mol_type = other DNA
                         note = enterovirus CVA16 guide DNA
                         organism = synthetic construct
SEQUENCE: 21
ttgggcttgg ctacga                                                      16

SEQ ID NO: 22            moltype = DNA  length = 16
FEATURE                  Location/Qualifiers
source                   1..16
                         mol_type = other DNA
                         note = enterovirus CVA16 molecular beacon
                         organism = synthetic construct
SEQUENCE: 22
tcgtagccaa gcccaa                                                      16

SEQ ID NO: 23            moltype = DNA  length = 16
```

-continued

```
FEATURE                 Location/Qualifiers
source                  1..16
                        mol_type = other DNA
                        note = enterovirus CVA16 guide DNA
                        organism = synthetic construct
SEQUENCE: 23
ttcacgtttg tcgtag                                                16

SEQ ID NO: 24           moltype = DNA  length = 16
FEATURE                 Location/Qualifiers
source                  1..16
                        mol_type = other DNA
                        note = enterovirus CVA16 guide DNA
                        organism = synthetic construct
SEQUENCE: 24
ccaagcccaa tggtga                                                16

SEQ ID NO: 25           moltype = DNA  length = 16
FEATURE                 Location/Qualifiers
source                  1..16
                        mol_type = other DNA
                        note = enterovirus CVA16 guide DNA
                        organism = synthetic construct
SEQUENCE: 25
tagctcacca ttgggc                                                16

SEQ ID NO: 26           moltype = DNA  length = 31
FEATURE                 Location/Qualifiers
source                  1..31
                        mol_type = other DNA
                        note = enterovirus universal EVU RPA primer
                        organism = synthetic construct
SEQUENCE: 26
ccacatgcca gtgggcagcc tgtcgtaacg g                               31

SEQ ID NO: 27           moltype = DNA  length = 31
FEATURE                 Location/Qualifiers
source                  1..31
                        mol_type = other DNA
                        note = Enterovirus universal EVU RPA primer
                        organism = synthetic construct
SEQUENCE: 27
gatggccaat ccaatagcga gatggcaaca a                               31

SEQ ID NO: 28           moltype = DNA  length = 33
FEATURE                 Location/Qualifiers
source                  1..33
                        mol_type = other DNA
                        note = enterovirus EV71 RPA primer
                        organism = synthetic construct
SEQUENCE: 28
tgctcgtgtc atctaccacc gcccaaggtt gtg                             33

SEQ ID NO: 29           moltype = DNA  length = 30
FEATURE                 Location/Qualifiers
source                  1..30
                        mol_type = other DNA
                        note = enterovirus EV71 RPA primer
                        organism = synthetic construct
SEQUENCE: 29
gcatctaagg ataccgccac aatcaccagg                                 30

SEQ ID NO: 30           moltype = DNA  length = 30
FEATURE                 Location/Qualifiers
source                  1..30
                        mol_type = other DNA
                        note = enterovirus CVA6 RPA primer
                        organism = synthetic construct
SEQUENCE: 30
gccactttgc catccgaaca gtcagtgaat                                 30

SEQ ID NO: 31           moltype = DNA  length = 31
FEATURE                 Location/Qualifiers
source                  1..31
                        mol_type = other DNA
                        note = enterovirus CVA6 RPA primer
                        organism = synthetic construct
SEQUENCE: 31
taatccgtgg tggttatgct tgcacggtcg g                               31
```

```
SEQ ID NO: 32          moltype = DNA  length = 35
FEATURE                Location/Qualifiers
source                 1..35
                       mol_type = other DNA
                       note = enterovirus CVA10 RPA primer
                       organism = synthetic construct
SEQUENCE: 32
actttcggcc agcacccgga gacctcaaac acaac                            35

SEQ ID NO: 33          moltype = DNA  length = 28
FEATURE                Location/Qualifiers
source                 1..28
                       mol_type = other DNA
                       note = enterovirus CVA10 RPA primer
                       organism = synthetic construct
SEQUENCE: 33
ctcgggaccc aggccctcac atgcttaa                                    28

SEQ ID NO: 34          moltype = DNA  length = 31
FEATURE                Location/Qualifiers
source                 1..31
                       mol_type = other DNA
                       note = enterovirus CVA16 RPA primer
                       organism = synthetic construct
SEQUENCE: 34
gtacacagaa cacagacggt tatgttaact g                                31

SEQ ID NO: 35          moltype = DNA  length = 30
FEATURE                Location/Qualifiers
source                 1..30
                       mol_type = other DNA
                       note = enterovirus CVA16 RPA primer
                       organism = synthetic construct
SEQUENCE: 35
aacgaatctc tggaagtggg tttcggagcc                                  30

SEQ ID NO: 36          moltype = AA  length = 778
FEATURE                Location/Qualifiers
source                 1..778
                       mol_type = protein
                       note = PfAgo protein
                       organism = synthetic construct
SEQUENCE: 36
MHHHHHHSMK AIVVINLVKI NKKIIPDKIY VYRLFNDPEE ELQKEGYSIY RLAYENVGIV  60
IDPENLIIAT TKELEYEGEF IPEGEISFSE LRNDYQSKLV LRLLKENGIG EYELSKLLRK  120
FRKPKTFGDY KVIPSVEMSV IKHDEDFYLV IHIIHQIQSM KTLWELVNKD PKELEEFLMT  180
HKENLMLKDI ASPLKTVYKP CFEEYTKKPK LDHNQEIVKY WYNYHIERYW NTPEAKLEFY  240
RKFGQVDLKQ PAILAKFASK IKKNKNYKIY LLPQLVVPTY NAEQLESDVA KEILEYTKLM  300
PEERKELLEN ILAEVDSDII DKSLSEIEVE KIAQELENKI RVRDDKGNSV PISQLNVQKS  360
QLLLWTNYSR KYPVILPYEV PEKFRKIREI PMFIILDSGL LADIQNFATN EFRELVKSMY  420
YSLAKKYNSL AKKARSTNEI GLPFLDFRGK EKVITEDLNS DKGIIEVVEQ VSSFMKGKEL  480
GLAFIAARNK LSSEKFEEIK RRLFNLNVIS QVVNEDTLKN KRDKYDRNRL DLFVRHNLLF  540
QVLSKLGVKY YVLDYRFNYD YIIGIDVAPM KRSEGYIGGS AVMFDSQGYI RKIVPIKIGE  600
QRGESVDMNE FFKEMVDKFK EFNIKLDNKK ILLLRDGRIT NNEEEGLKYI SEMFDIEVVT  660
MDVIKNHPVR AFANMKMYFN LGGAIYLIPH KLKQAKGTPI PIKLAKKRII KNGKVEKQSI  720
TRQDVLDIFI LTRLNYGSIS ADMRLPAPVH YAHKFANAIR NEWKIKEEFL AEGFLYFV    778

SEQ ID NO: 37          moltype = AA  length = 77
FEATURE                Location/Qualifiers
source                 1..77
                       mol_type = protein
                       note = enterovirus universal EVU
                       organism = synthetic construct
SEQUENCE: 37
CCAGGGGGTG TCGTAAGGCA ATCTGGCGGA ACCGACTCTT TGGGTGTCCG TGTTTCTTTT  60
ATTATGGCTG CTTATGG                                                77

SEQ ID NO: 38          moltype = AA  length = 95
FEATURE                Location/Qualifiers
source                 1..95
                       mol_type = protein
                       note = enterovirus universal EVU
                       organism = synthetic construct
SEQUENCE: 38
CCAGTGGGTA GTCTGTCGTA ACGGGCAACT CTGCAGCGGA ACCGACTACT TTGGGTGTCC  60
GTGTTTCCAT TTATTCTTAT ACTGGCTGCT TATGG                            95

SEQ ID NO: 39          moltype = AA  length = 97
```

-continued

```
FEATURE                 Location/Qualifiers
source                  1..97
                        mol_type = protein
                        note = enterovirus universal EVU
                        organism = synthetic construct
SEQUENCE: 39
ATCCAGGGGG TGGTGTGTCG TAATGGGCAA CTCTGCAGCG GAACCGACTA CTTTGGGTGT  60
CCGTGTTTCC TTTTATTCTT ACACTGGCTG CTTATGG                           97

SEQ ID NO: 40           moltype = AA  length = 102
FEATURE                 Location/Qualifiers
source                  1..102
                        mol_type = protein
                        note = enterovirus universal EVU
                        organism = synthetic construct
SEQUENCE: 40
CCACGAGCCA GTGGGCAGTC TGTCGTAACG GGCAACTCTG CAGCGGAACC GACTACTTTG  60
GGTGACCGTG TTTCCTTTTA TCTCTAAACT GGCTGCTTAT GG                     102

SEQ ID NO: 41           moltype = AA  length = 97
FEATURE                 Location/Qualifiers
source                  1..97
                        mol_type = protein
                        note = enterovirus universal EVU
                        organism = synthetic construct
SEQUENCE: 41
AGCCAGCGAG TGGTGTGTCG TAATGGGCAA CTCTGCAGCG GAACCGACTA CTTTGGGTGT  60
CCGTGTTTCC TTTTATTTTT ATATTGGCTG CTTATGG                           97

SEQ ID NO: 42           moltype = AA  length = 97
FEATURE                 Location/Qualifiers
source                  1..97
                        mol_type = protein
                        note = enterovirus universal EVU
                        organism = synthetic construct
SEQUENCE: 42
AACCAGTGGG CAGTCTGTCG TAACGGGCAA CTCTGCAGCG GAACCGACTA CTTTGGGTGA  60
CCGTGTTTCC TTTTATACTT AAACTGGCTG CTTATGG                           97

SEQ ID NO: 43           moltype = AA  length = 97
FEATURE                 Location/Qualifiers
source                  1..97
                        mol_type = protein
                        note = enterovirus universal EVU
                        organism = synthetic construct
SEQUENCE: 43
AACCAGTGGG TAGCTTGTCG TAACGCGCAA GTCTGTGGCG GAACCGACTA CTTTGGGTGT  60
CCGTGTTTCT TTTTATTTTT ATCATGGCTG CTTATGG                           97

SEQ ID NO: 44           moltype = AA  length = 97
FEATURE                 Location/Qualifiers
source                  1..97
                        mol_type = protein
                        note = enterovirus universal EVU
                        organism = synthetic construct
SEQUENCE: 44
ATCCAGGGGG CAGTGTGTCG TAACGGGCAA CTCTGCAGCG GAACCGACTA CTTTGGGTGT  60
CCGTGTTTCC TTTTATTCTT ATTATGGCTG CTTATGG                           97

SEQ ID NO: 45           moltype = AA  length = 97
FEATURE                 Location/Qualifiers
source                  1..97
                        mol_type = protein
                        note = enterovirus universal EVU
                        organism = synthetic construct
SEQUENCE: 45
AGCCAGTGGG CGGTCTGTCG TAACGGGCAA CTCTGCAGCG GAACCGACTA CTTTGGGTGT  60
CCGTGTTTCC CTTTATTCTT GATGTGGCTG CTTATGG                           97

SEQ ID NO: 46           moltype = AA  length = 97
FEATURE                 Location/Qualifiers
source                  1..97
                        mol_type = protein
                        note = enterovirus universal EVU
                        organism = synthetic construct
SEQUENCE: 46
ACCCAGGAGG TAGTGTGTCG TAACGGGCAA CTCTGCAGCG GAACCGACTA CTTTGGGTGT  60
CCGTGTTTCT TTTTATTCTC ACATTGGCTG CTTATGG                           97
```

-continued

```
SEQ ID NO: 47          moltype = AA  length = 97
FEATURE                Location/Qualifiers
source                 1..97
                       mol_type = protein
                       note = enterovirus universal EVU
                       organism = synthetic construct
SEQUENCE: 47
AAACCAGTGA TTGGCCTGTC GTAACGCGCA AGCCCGTGGC GGAACCGACT ACTTTGGGTG  60
TCCGTGTTTC CTTTTATTTT ATTGTGGCTG CTTATGG                           97

SEQ ID NO: 48          moltype = AA  length = 94
FEATURE                Location/Qualifiers
source                 1..94
                       mol_type = protein
                       note = enterovirus universal EVU
                       organism = synthetic construct
SEQUENCE: 48
CAGTGACTGG CTTGTCGTAA CGCGCAAGTC CGTGGCGGAA CCGACTACTT TGGGTGTCCG  60
TGTTTCCTGT TATTTTAATG AGGGCGGCTT AGGG                              94

SEQ ID NO: 49          moltype = AA  length = 102
FEATURE                Location/Qualifiers
source                 1..102
                       mol_type = protein
                       note = enterovirus universal EVU
                       organism = synthetic construct
SEQUENCE: 49
TACCAGTGGA GTAGTCTGTC GTACGCGCAA CGTCTGCAGG CGGAACCGAC TACTTTGGGT  60
GTCCGTGTTT CCTTGTTATT CTTTATACAT GGCTGCTTAT GG                     102

SEQ ID NO: 50          moltype = AA  length = 102
FEATURE                Location/Qualifiers
source                 1..102
                       mol_type = protein
                       note = enterovirus universal EVU
                       organism = synthetic construct
SEQUENCE: 50
CCACATGCCA GTGGGCAGCC TGTCGTAACG GGTAACTCTG CAGCGGAACC GACTACTTTG  60
GGTGTCCGTG TTTCCTTTTA CTCTTACATT GGCTGCTTAT GG                     102

SEQ ID NO: 51          moltype = AA  length = 96
FEATURE                Location/Qualifiers
source                 1..96
                       mol_type = protein
                       note = enterovirus universal EVU
                       organism = synthetic construct
SEQUENCE: 51
GCCAGTGGGC AGTCTGTCGT AATGGGCAAC TCTGCAGCGG AACCGACTAC TTTGGGTGTC  60
CGTGTTTCTT TTTATCTAAT TCCTGGCTGC TTATGG                            96

SEQ ID NO: 52          moltype = AA  length = 97
FEATURE                Location/Qualifiers
source                 1..97
                       mol_type = protein
                       note = enterovirus universal EVU
                       organism = synthetic construct
SEQUENCE: 52
ATCCAGGGGG TGGTGTGTCG TAATGGGTAA CTCTGCAGCG GAACCGACTA CTTTGGGTGT  60
CCGTGTTTCC TTTTATTCTT ACACTGGCTG CTTATGG                           97

SEQ ID NO: 53          moltype = AA  length = 97
FEATURE                Location/Qualifiers
source                 1..97
                       mol_type = protein
                       note = enterovirus universal EVU
                       organism = synthetic construct
SEQUENCE: 53
AACCAGTGGG TAGCTTGTCG TAACGCGTAA GTCTGTGGCG GAACCGACTA CTTTGGGTGT  60
CCGTGTTTCT TTTTATTTTT ATCATGGCTG CTTATGG                           97

SEQ ID NO: 54          moltype = AA  length = 97
FEATURE                Location/Qualifiers
source                 1..97
                       mol_type = protein
                       note = enterovirus universal EVU
                       organism = synthetic construct
SEQUENCE: 54
AACCAGTGGG TAGCTTGTCG TAACGCGCAA GTCTGTGGCG GAACCGACTA CTTTGGGTGT  60
CCGTGTTTCT TTTTATTTTT ATCATGGCTG CTTATGG                           97
```

-continued

```
SEQ ID NO: 55          moltype = AA  length = 95
FEATURE                Location/Qualifiers
source                 1..95
                       mol_type = protein
                       note = enterovirus universal EVU
                       organism = synthetic construct
SEQUENCE: 55
ACCATGATTG GCCTGTCGTA ATGCGCAAGT CTGTGGCGGA ACCGACTACT TTGGGTGTCC  60
GTGTTTCCTT TTATTTTTAC ATTGGCTGCT TATGG                             95

SEQ ID NO: 56          moltype = AA  length = 97
FEATURE                Location/Qualifiers
source                 1..97
                       mol_type = protein
                       note = enterovirus universal EVU
                       organism = synthetic construct
SEQUENCE: 56
AACCAGTGGG TAGCTTGTCG TAACGCGCAA GTCTGTGGCG GAACCGACTA CTTTGGGTGT  60
CCGTGTTTCT TTTTATTTTT ATCATGGCTG CTTATGG                           97

SEQ ID NO: 57          moltype = AA  length = 94
FEATURE                Location/Qualifiers
source                 1..94
                       mol_type = protein
                       note = enterovirus universal EVU
                       organism = synthetic construct
SEQUENCE: 57
CAGGGGGTGG CGTGTCGTAA CGGGCAACTC TGCAGCGGAA CCGACTACTT TGGGTGTCCG  60
TGTTTCCTTT TATTTTTATA TTGGCTGCTT ATGG                              94

SEQ ID NO: 58          moltype = AA  length = 97
FEATURE                Location/Qualifiers
source                 1..97
                       mol_type = protein
                       note = enterovirus universal EVU
                       organism = synthetic construct
SEQUENCE: 58
AACCAGTGGG TAGCTTGTCG TAACGCGCAA GTCTGTGGCG GAACCGACTA CTTTGGGTGT  60
CCGTGTTTCT TTTTATTTTT ATCATGGCTG CTTATGG                           97

SEQ ID NO: 59          moltype = AA  length = 96
FEATURE                Location/Qualifiers
source                 1..96
                       mol_type = protein
                       note = enterovirus universal EVU
                       organism = synthetic construct
SEQUENCE: 59
GCCAGTGGGC GGTCTGTCGT AATGGGTAAC TCTGCAGCGG AACCGACTAC TTTGGGTGTC  60
CGTGTTTCCT TTTATTCTTA CATTGGCTGC TTATGG                            96

SEQ ID NO: 60          moltype = AA  length = 94
FEATURE                Location/Qualifiers
source                 1..94
                       mol_type = protein
                       note = enterovirus EV71
                       organism = synthetic construct
SEQUENCE: 60
AGTTTTTCAA AACCCAGCCT ATCTATGTAG AGCTAGCGAG TATTACCCAG CCAGGTACCA  60
ATCACATCTC ATGCTCGCAC AGGGTCACTC AGAA                              94

SEQ ID NO: 61          moltype = AA  length = 96
FEATURE                Location/Qualifiers
source                 1..96
                       mol_type = protein
                       note = enterovirus EV71
                       organism = synthetic construct
SEQUENCE: 61
AGTTTTTCAA AACCCAGCCT GATCTATGTA GAGGCTAGCG AGTGTTACCC AGCCAGGTAC  60
CAATCACATC TCATGCTCGC ACAGGGTCAC TCAGAA                            96

SEQ ID NO: 62          moltype = AA  length = 96
FEATURE                Location/Qualifiers
source                 1..96
                       mol_type = protein
                       note = enterovirus EV71
                       organism = synthetic construct
SEQUENCE: 62
AGTTTTTCGA AACCCAGCCT AGTCTATGTA GATGCTAGCG AGTATTACCC AGCCAGGTAC  60
```

-continued

```
CAATCACATC TCATGCTCGC ACAGGGTCAC TCAGAA                      96

SEQ ID NO: 63           moltype = AA  length = 96
FEATURE                 Location/Qualifiers
source                  1..96
                        mol_type = protein
                        note = enterovirus EV71
                        organism = synthetic construct
SEQUENCE: 63
AGTTTTTCAA AACCCAGCCT AATCTATGTA GATGCTAGCG AGTATTACCC AGCCAGGTAC  60
CAATCACATC TCATGCTCGC ACAGGGTCAC TCAGAA                      96

SEQ ID NO: 64           moltype = AA  length = 96
FEATURE                 Location/Qualifiers
source                  1..96
                        mol_type = protein
                        note = enterovirus EV71
                        organism = synthetic construct
SEQUENCE: 64
AGTTTTTCGA AACCCAGCCT AGTCTATGTA GATGCTAGCG AGTATTACCC AGCCAGGTAC  60
CAATCACATC TCATGCTCGC ACAGGGTCAC TCAGAA                      96

SEQ ID NO: 65           moltype = AA  length = 96
FEATURE                 Location/Qualifiers
source                  1..96
                        mol_type = protein
                        note = enterovirus EV71
                        organism = synthetic construct
SEQUENCE: 65
AGTTTTTCAA AACCCAGCCT GATCTATGTA GAGGCTAGCG AGTATTACCC AGCCAGGTAC  60
CAATCACATC TCATGCTCGC ACAGGGTCAC TCAGAA                      96

SEQ ID NO: 66           moltype = AA  length = 96
FEATURE                 Location/Qualifiers
source                  1..96
                        mol_type = protein
                        note = enterovirus EV71
                        organism = synthetic construct
SEQUENCE: 66
AGTTTCTCGA AACCCAGCCT AATCTATGTA GATGCTAGCG AGTATTACCC AGCCAGGTAT  60
CAATCACATC TTATGCTCGC ACAGGGCCAC TCAGAG                      96

SEQ ID NO: 67           moltype = AA  length = 96
FEATURE                 Location/Qualifiers
source                  1..96
                        mol_type = protein
                        note = enterovirus EV71
                        organism = synthetic construct
SEQUENCE: 67
AGTTTTTCAA AACCCAGCCT GATCTATGTA GATGCTAGCG AGTATTACCC AGCCAGGTAC  60
CAATCACATC TCATGCTCGC ACAGGGTCAC TCAGAA                      96

SEQ ID NO: 68           moltype = AA  length = 96
FEATURE                 Location/Qualifiers
source                  1..96
                        mol_type = protein
                        note = enterovirus EV71
                        organism = synthetic construct
SEQUENCE: 68
AGTTTTTCAA AACCCAGCCT AATCTATGTA GATGCTAGCG AGTATTACCC AGCCAGGTAC  60
CAATCACATC TCATGCTTGC ACAGGGTCAC TCAGAA                      96

SEQ ID NO: 69           moltype = AA  length = 96
FEATURE                 Location/Qualifiers
source                  1..96
                        mol_type = protein
                        note = enterovirus EV71
                        organism = synthetic construct
SEQUENCE: 69
AGCTTTTCAA AACCCAGCCT GATCTATGTA GAGGCTAGCG AGTATTACCC GGCCAGGTAC  60
CAATCACATC TCATGCTCGC GCAGGGTCAC TCAGAA                      96

SEQ ID NO: 70           moltype = AA  length = 96
FEATURE                 Location/Qualifiers
source                  1..96
                        mol_type = protein
                        note = enterovirus EV71
                        organism = synthetic construct
SEQUENCE: 70
```

-continued

```
AGTTTTTCAA AACCCAGCCT GATCTATGTA GAGGCTAGCG AGTATTACCC AGCCAGGTAC  60
CAATCACATC TCATGCTCGC ACAGGGTCAC TCAGAA                            96

SEQ ID NO: 71          moltype = AA  length = 96
FEATURE                Location/Qualifiers
source                 1..96
                       mol_type = protein
                       note = enterovirus EV71
                       organism = synthetic construct
SEQUENCE: 71
AGTTTTTCAA AACCCAGCCT GATCTATGTA GAGGCTAGCG AGTATTACCC AGCCAGGTAC  60
CAATCACATC TCATGCTCGC ACAGGGTCAC TCAGAA                            96

SEQ ID NO: 72          moltype = AA  length = 96
FEATURE                Location/Qualifiers
source                 1..96
                       mol_type = protein
                       note = enterovirus EV71
                       organism = synthetic construct
SEQUENCE: 72
AGTTTTTCAA AACCCAGCCT GATCTATGTA GAGGCTAGCG AGTATTACCC AGCCAGGTAC  60
CAATCACATC TCATGCTCGC ACAGGGTCAC TCAGAA                            96

SEQ ID NO: 73          moltype = AA  length = 96
FEATURE                Location/Qualifiers
source                 1..96
                       mol_type = protein
                       note = enterovirus EV71
                       organism = synthetic construct
SEQUENCE: 73
AGTTTTTCAA AACCCAGCCT GATCTATGTG GAGGCTAGCG AGTATTACCC AGCCAGGTAC  60
CAATCACATC TCATGCTCGC ACAGGGTCAC TCAGAA                            96

SEQ ID NO: 74          moltype = AA  length = 96
FEATURE                Location/Qualifiers
source                 1..96
                       mol_type = protein
                       note = enterovirus EV71
                       organism = synthetic construct
SEQUENCE: 74
AGTTTTTCAA AACCCAGCCT GATCTATGTA GAGGCTAGCG AGTATTACCC AGCCAGGTAC  60
CAATCACATC TCATGCTCGC ACAGGGTCAC TCAGAA                            96

SEQ ID NO: 75          moltype = AA  length = 96
FEATURE                Location/Qualifiers
source                 1..96
                       mol_type = protein
                       note = enterovirus EV71
                       organism = synthetic construct
SEQUENCE: 75
AGTTTTTCAA AACCCAGCCT AATCTATGTA GATGCTAGCG AGTATTACCC AGCCAGGTAC  60
CAATCACATC TCATGCTCGC ACAGGGTCAC TCAGAG                            96

SEQ ID NO: 76          moltype = AA  length = 96
FEATURE                Location/Qualifiers
source                 1..96
                       mol_type = protein
                       note = enterovirus CVA6
                       organism = synthetic construct
SEQUENCE: 76
GAACAGTCAG TGAATCTACC ACCGGGAAAA ACTCCACGTT CGGGTGTACA TGAGATTAAG  60
CACGTGAGAG CTTGGGTACC TAGACCCCTT CGATCC                            96

SEQ ID NO: 77          moltype = AA  length = 94
FEATURE                Location/Qualifiers
source                 1..94
                       mol_type = protein
                       note = enterovirus CVA6
                       organism = synthetic construct
SEQUENCE: 77
GAACAGTGAA TCTACCACCG GGAAAAACGT CCACGTTCGG GTGTACATGA GAATTAAGCA  60
CGTGAGAGCT TGGGTACCTA GACCCCTTCG ATCC                              94

SEQ ID NO: 78          moltype = AA  length = 94
FEATURE                Location/Qualifiers
source                 1..94
                       mol_type = protein
                       note = enterovirus CVA6
                       organism = synthetic construct
```

-continued

```
SEQUENCE: 78
GAACAGTGAA TCTACCACCG GGAAAAACAT CCACGTTCGG GTGTACATGA GGATTAAGCA  60
CGTGAGAGCT TGGGTACCTA GACCCCTTCG ATCC                              94

SEQ ID NO: 79          moltype = AA  length = 94
FEATURE                Location/Qualifiers
source                 1..94
                       mol_type = protein
                       note = enterovirus CVA6
                       organism = synthetic construct
SEQUENCE: 79
GGACAGTGAA TCTACCACCG GGAAAAACGT CCACGTTCGG GTGTACATGA GAATTAAGCA  60
CGTGAGGGCT TGGGTACCTA GACCCCTTCG ATCC                              94

SEQ ID NO: 80          moltype = AA  length = 94
FEATURE                Location/Qualifiers
source                 1..94
                       mol_type = protein
                       note = enterovirus CVA6
                       organism = synthetic construct
SEQUENCE: 80
GAACAGTGAG TCCACTACCG GGAAAAACAT CCACGTTCGG GTGTACATGA GGATCAAACA  60
CGTGAGAGCT TGGGTGCCTA GGCCCCTCCG ATCC                              94

SEQ ID NO: 81          moltype = AA  length = 94
FEATURE                Location/Qualifiers
source                 1..94
                       mol_type = protein
                       note = enterovirus CVA6
                       organism = synthetic construct
SEQUENCE: 81
GAACAGTGAG TCCACTACCG GGAAAAACAT CCACGTTCGG GTGTACATGA GAATCAAACA  60
CGTGAGAGCT TGGGTGCCTA GGCCCCTCCG ATCT                              94

SEQ ID NO: 82          moltype = AA  length = 94
FEATURE                Location/Qualifiers
source                 1..94
                       mol_type = protein
                       note = enterovirus CVA6
                       organism = synthetic construct
SEQUENCE: 82
GAACAGTGAG TCCACTACCG GGAAAAACAT CCACGTTCGG GTGTACATGA GGATCAAACA  60
CGTGAGAGCT TGGGTGCCTA GGCCCCTCCG ATCC                              94

SEQ ID NO: 83          moltype = AA  length = 94
FEATURE                Location/Qualifiers
source                 1..94
                       mol_type = protein
                       note = enterovirus CVA6
                       organism = synthetic construct
SEQUENCE: 83
GAACAGTGAA TCTACCACCG GGAAAAACGT CCACGTTCGG GTGTACATGA GAATTAAGCA  60
TGTGAGAGCT TGGGTACCTA GACCCCTTCG ATCC                              94

SEQ ID NO: 84          moltype = AA  length = 94
FEATURE                Location/Qualifiers
source                 1..94
                       mol_type = protein
                       note = enterovirus CVA6
                       organism = synthetic construct
SEQUENCE: 84
GAACAGTGAA GCTACCACCG GGAAAAACGT CCACGTTCGG GTGTACATGA GAATTAAGCA  60
CGTGAGAGCC TGGGTACCTA GACCCCTTCG ATCC                              94

SEQ ID NO: 85          moltype = AA  length = 94
FEATURE                Location/Qualifiers
source                 1..94
                       mol_type = protein
                       note = enterovirus CVA6
                       organism = synthetic construct
SEQUENCE: 85
GAACAGTGAA TCTACCACCG GGAAGAACGT CCACGTTCGG GTGTACATGA GGATTAAGCA  60
CGTGAGAGCT TGGGTACCTA GACCCCTTCG ATCC                              94

SEQ ID NO: 86          moltype = AA  length = 94
FEATURE                Location/Qualifiers
source                 1..94
                       mol_type = protein
                       note = enterovirus CVA6
```

-continued

```
                         organism = synthetic construct
SEQUENCE: 86
GAACAGTGAA TCTACCACCG GGAAAAACAT CCACGTTCGG GTGTACATGA GAATTAAGCA  60
CGTGAGAGCT TGGGTACCTA GACCCCTTCG ATCC                              94

SEQ ID NO: 87            moltype = AA  length = 94
FEATURE                  Location/Qualifiers
source                   1..94
                         mol_type = protein
                         note = enterovirus CVA6
                         organism = synthetic construct
SEQUENCE: 87
GAACAGTGAA TCTACCACCG GGAAAAACAT CCACGTTCGG GTGTACATGA GAATTAAGCA  60
CGTGAGAGCT TGGGTACCTA GACCCCTTCG ATCC                              94

SEQ ID NO: 88            moltype = AA  length = 94
FEATURE                  Location/Qualifiers
source                   1..94
                         mol_type = protein
                         note = enterovirus CVA6
                         organism = synthetic construct
SEQUENCE: 88
GAACAGTGAA TCTACCACCG GGAAAAACGT CCACGTTCGG GTGTACATGA GAATTAAGCA  60
CGTGAGAGCT TGGGTACCTA GACCCCTTCG ATCC                              94

SEQ ID NO: 89            moltype = AA  length = 94
FEATURE                  Location/Qualifiers
source                   1..94
                         mol_type = protein
                         note = enterovirus CVA6
                         organism = synthetic construct
SEQUENCE: 89
GAACAGTGAA TCTACCACCG GGAAAAACGT CCACGTTCGG GTGTACATGA GAATTAAGCA  60
CGTGAGAGCT TGGGTACCTA GACCCCTTCG ATCC                              94

SEQ ID NO: 90            moltype = AA  length = 94
FEATURE                  Location/Qualifiers
source                   1..94
                         mol_type = protein
                         note = enterovirus CVA6
                         organism = synthetic construct
SEQUENCE: 90
GAACAGTGAA TCTACCACCG GGAAAAACGT CCACATTCGG GTGTACATGA GAATTAAGCA  60
CGTGAGAGCT TGGGTACCTA GACCCCTTCG ATCC                              94

SEQ ID NO: 91            moltype = AA  length = 94
FEATURE                  Location/Qualifiers
source                   1..94
                         mol_type = protein
                         note = enterovirus CVA6
                         organism = synthetic construct
SEQUENCE: 91
GAACAGTGAA TCTACCACCG GGAAAAACGT CCACGTTCGG GTGTACATGA GAATTAAGCA  60
CGTGAGAGCT TGGGTACCTA GACCCCTTCG ATCC                              94

SEQ ID NO: 92            moltype = AA  length = 98
FEATURE                  Location/Qualifiers
source                   1..98
                         mol_type = protein
                         note = enterovirus CVA10
                         organism = synthetic construct
SEQUENCE: 92
ACGGATTGTG CCCAAACAAT ATGATGGGCA CTTTTGCAGT GAGAGTTGTT AGAGGGAGGC  60
AAGCAACTAA AACTACAGAC TAGAGTGTAC ATGAAGCT                          98

SEQ ID NO: 93            moltype = AA  length = 100
FEATURE                  Location/Qualifiers
source                   1..100
                         mol_type = protein
                         note = enterovirus CVA10
                         organism = synthetic construct
SEQUENCE: 93
ACGGATTGTG CCCAAACAAC ATGATGGGCA CTTTTGCAGT GAGAGTTGTT AGTAGGGAGG  60
CAAGCCAACT GAAACTGCAG ACTAGAGTGT ACATGAAGCT                        100

SEQ ID NO: 94            moltype = AA  length = 100
FEATURE                  Location/Qualifiers
source                   1..100
                         mol_type = protein
```

-continued

```
                        note = enterovirus CVA10
                        organism = synthetic construct
SEQUENCE: 94
ATGGATTGTG CCCAAACAAT ATGATGGGCA CTTTTGCAGT GAGAGTTGTC AGTAGGGAGG  60
CAAGCCAACT AAAACTACAG ACCAGAGTGT ACATGAAGCT                        100

SEQ ID NO: 95           moltype = AA  length = 100
FEATURE                 Location/Qualifiers
source                  1..100
                        mol_type = protein
                        note = enterovirus CVA10
                        organism = synthetic construct
SEQUENCE: 95
ACGGGTTGTG CCCAAACAAT ATGATGGGCA CTTTTGCGGT GAGAATTGTT AGCAAGAAGG  60
CAAGTCAACT AAAACTACAG ACTAGAGTGT ACATGAAGCT                        100

SEQ ID NO: 96           moltype = AA  length = 100
FEATURE                 Location/Qualifiers
source                  1..100
                        mol_type = protein
                        note = enterovirus CVA10
                        organism = synthetic construct
SEQUENCE: 96
ACGGGTTGTG CCCAAACAAT ATGATGGGCA CTTTTGCGGT GAGAATTGTT AGCAAGAAGG  60
CAAGTCAACT AAAACTACAG ACTAGAGTGT ACATGAAGCT                        100

SEQ ID NO: 97           moltype = AA  length = 100
FEATURE                 Location/Qualifiers
source                  1..100
                        mol_type = protein
                        note = enterovirus CVA10
                        organism = synthetic construct
SEQUENCE: 97
ACGGATTGTG TCCAAACAAT ATGATGGGCA CCTTTGCAGT GAGAGTTGTT AGTAGGGAGG  60
CAAGCCAACT AAAACTACAG ACTAGAGTGT ACATGAAGCT                        100

SEQ ID NO: 98           moltype = AA  length = 100
FEATURE                 Location/Qualifiers
source                  1..100
                        mol_type = protein
                        note = enterovirus CVA10
                        organism = synthetic construct
SEQUENCE: 98
ACGGATTGTG CCCAAACAAT ATGATGGGCA CTTTTGCAGT GAGAGTTGTT AGCAGGGAGG  60
CAAGTCAACT AAAACTACAG ACCAGAGTGT ACATGAAGCT                        100

SEQ ID NO: 99           moltype = AA  length = 100
FEATURE                 Location/Qualifiers
source                  1..100
                        mol_type = protein
                        note = enterovirus CVA10
                        organism = synthetic construct
SEQUENCE: 99
ACGGATTGTG TCCAAACAAT ATGATGGGCA CTTTTGCAGT GAGAGTTGTT AGTAGGGAGG  60
CAAGCCAACT AAAACTACAG ACTAGAGTGT ACATGAAGCT                        100

SEQ ID NO: 100          moltype = AA  length = 100
FEATURE                 Location/Qualifiers
source                  1..100
                        mol_type = protein
                        note = enterovirus CVA10
                        organism = synthetic construct
SEQUENCE: 100
ACGGATTGTG CCCAAACAAC ATGATGGGCA CTTTTGCAGT GAGAGTTGTT AGTAGGAAGG  60
CAAGCCAACT AAAACTACAG ACTAGAGTAT ACATGAAGCT                        100

SEQ ID NO: 101          moltype = AA  length = 100
FEATURE                 Location/Qualifiers
source                  1..100
                        mol_type = protein
                        note = enterovirus CVA10
                        organism = synthetic construct
SEQUENCE: 101
ACGGGTTGTG CCCAAACAAT ATGATGGGCA CTTTTGCGGT GAGAATTGTT AGCAAGAAGG  60
CAAGTCAACT AAAACTACAG ACTAGAGTGT ACATGAAGCT                        100

SEQ ID NO: 102          moltype = AA  length = 100
FEATURE                 Location/Qualifiers
source                  1..100
```

-continued

```
                        mol_type = protein
                        note = enterovirus CVA10
                        organism = synthetic construct
SEQUENCE: 102
ACGGATTGTG CCCAAACAAT ATGATGGGCA CTTTTGCAGT GAGAGTTGTT AGTAGGGAGG  60
CAAGTCAATT AAAACTACAG ACTAGAGTGT ACATGAAGCT                        100

SEQ ID NO: 103          moltype = AA  length = 100
FEATURE                 Location/Qualifiers
source                  1..100
                        mol_type = protein
                        note = enterovirus CVA10
                        organism = synthetic construct
SEQUENCE: 103
ACGGATTGTG CCCAAACAAT ATGATGGGCA CTTTTGCAGT GAGAGTTGTT AGTAGGGAGG  60
CAAGTCAATT AAAACTACAG ACTAGAGTGT ACATGAAGCT                        100

SEQ ID NO: 104          moltype = AA  length = 100
FEATURE                 Location/Qualifiers
source                  1..100
                        mol_type = protein
                        note = enterovirus CVA10
                        organism = synthetic construct
SEQUENCE: 104
ACGGATTGTG TCCAAACAAT ATGATGGGCA CTTTTGCAGT AAGAGTTGTT AGTAGGGAGG  60
CAAGCCAACT AAAACTACAG ACTAGAGTGT ACATGAAGCT                        100

SEQ ID NO: 105          moltype = AA  length = 100
FEATURE                 Location/Qualifiers
source                  1..100
                        mol_type = protein
                        note = enterovirus CVA10
                        organism = synthetic construct
SEQUENCE: 105
ACGGATTGTG CCCAAACAAT ATGATGGGCA CTTTTGCAGT GAGAGTTGTT AGTAGGGAGG  60
CAAGCCAACT AAAACTGCAG ACTAGAGTGT ACATGAAGCT                        100

SEQ ID NO: 106          moltype = AA  length = 100
FEATURE                 Location/Qualifiers
source                  1..100
                        mol_type = protein
                        note = enterovirus CVA10
                        organism = synthetic construct
SEQUENCE: 106
ACGGATTGTG CCCAAACAAT ATGATGGGCA CTTTTGCAGT GAGAGTTGTT AGTAGGGAGG  60
CAAGCCAACT AAAACTGCAG ACTAGAGTGT ACATGAAGCT                        100

SEQ ID NO: 107          moltype = AA  length = 100
FEATURE                 Location/Qualifiers
source                  1..100
                        mol_type = protein
                        note = enterovirus CVA10
                        organism = synthetic construct
SEQUENCE: 107
ACGGATTGTG CCCAAACAAT ATGATGGGCA CTTTTGCAGT GAGAGTTGTT AGTAGAGAGG  60
CAAGTCAACT AAAACTACAG ACTAGAGTGT ACATGAAGCT                        100

SEQ ID NO: 108          moltype = AA  length = 97
FEATURE                 Location/Qualifiers
source                  1..97
                        mol_type = protein
                        note = enterovirus CVA16
                        organism = synthetic construct
SEQUENCE: 108
GCGGAAATGC GAGTTATTCA CCTACATGCG CTTTGATGCT GAATTCACAT TTGTCGTGCC  60
AAACCCAATG GTGAGTAGTC CCCCAATTAC TCAGTAC                           97

SEQ ID NO: 109          moltype = AA  length = 100
FEATURE                 Location/Qualifiers
source                  1..100
                        mol_type = protein
                        note = enterovirus CVA16
                        organism = synthetic construct
SEQUENCE: 109
GCGGAAATGC GAGTTATTCA CCTACATGCG CTTTGATGCT GAATTCACAT TTGTCGTAGC  60
CAAACCCAAT GGTGAGCTAG TCCCCCAATT ACTCCAGTAC                        100

SEQ ID NO: 110          moltype = AA  length = 100
FEATURE                 Location/Qualifiers
```

-continued

```
source                  1..100
                        mol_type = protein
                        note = enterovirus CVA16
                        organism = synthetic construct
SEQUENCE: 110
GCGGAAATGC GAGTTATTCA CCTACATGCG CTTTGATGCT GAATTCACAT TTGTCGTAGC  60
CAAACCCAAT GGTGAGCTAG TCCCCCAATT ACTCCAGTAC                        100

SEQ ID NO: 111          moltype = AA  length = 100
FEATURE                 Location/Qualifiers
source                  1..100
                        mol_type = protein
                        note = enterovirus CVA16
                        organism = synthetic construct
SEQUENCE: 111
GCGGAAGTGC GAGTTGTTCA CCTACATGCG CTTTGATGCT GAATTCACAT TTGTCGTGGC  60
TAAACCCAAT GGTGAGCTAG TCCCCCAATT ACTACAGTAC                        100

SEQ ID NO: 112          moltype = AA  length = 100
FEATURE                 Location/Qualifiers
source                  1..100
                        mol_type = protein
                        note = enterovirus CVA16
                        organism = synthetic construct
SEQUENCE: 112
GCGGAAATGC GAGTTATTCA CCTACATGCG CTTTGATGCT GAGTTCACAT TTGTCGTGGC  60
CAAACCCAAT GGTGTGCTAG TCCCCCAATT ACTCCAGTAC                        100

SEQ ID NO: 113          moltype = AA  length = 100
FEATURE                 Location/Qualifiers
source                  1..100
                        mol_type = protein
                        note = enterovirus CVA16
                        organism = synthetic construct
SEQUENCE: 113
GCGGAAATGC GAGTTATTCA CCTACATGCG CTTTGATGCT GAGTTCACAT TTGTCGTAGC  60
CAAACCCAAT GGTGAGCTAG TCCCCCAATT ACTCCAGTAC                        100

SEQ ID NO: 114          moltype = AA  length = 100
FEATURE                 Location/Qualifiers
source                  1..100
                        mol_type = protein
                        note = enterovirus CVA16
                        organism = synthetic construct
SEQUENCE: 114
GCGGAAATGC GAGTTATTCA CCTACATGCG CTTTGATGCT GAATTCACGT TTGTCGTGGC  60
CAAACCCAAT GGTGAGTTAG TCCCCCAATT ACTCCAGTAC                        100

SEQ ID NO: 115          moltype = AA  length = 100
FEATURE                 Location/Qualifiers
source                  1..100
                        mol_type = protein
                        note = enterovirus CVA16
                        organism = synthetic construct
SEQUENCE: 115
GCGGAAATGC GAGTTATTCA CCTACATGCG CTTTGATGCT GAATTCACGT TTGTCGTAGC  60
CAAACCTAAT GGTGAGTTAG TCCCCCAATT ACTCCAGTAC                        100

SEQ ID NO: 116          moltype = AA  length = 100
FEATURE                 Location/Qualifiers
source                  1..100
                        mol_type = protein
                        note = enterovirus CVA16
                        organism = synthetic construct
SEQUENCE: 116
GCGGAAATGC GAGTTATTCA CCTACATGCG CTTCGATGCT GAATTCACAT TCGTCGTAGC  60
CAAACCCAAT GGTGAGTTGG TTCCCCAATT ACTGCAGTAC                        100

SEQ ID NO: 117          moltype = AA  length = 100
FEATURE                 Location/Qualifiers
source                  1..100
                        mol_type = protein
                        note = enterovirus CVA16
                        organism = synthetic construct
SEQUENCE: 117
GCGGAAATGC GAGTTATTCA CCTACATGCG TTTTGATGCT GAATTCACAT TTGTCGTAGC  60
CAAACCCAAT GGTGAGCTAG TCCCCCAATT ACTCCAGTAC                        100

SEQ ID NO: 118          moltype = AA  length = 100
```

-continued

```
FEATURE                Location/Qualifiers
source                 1..100
                       mol_type = protein
                       note = enterovirus CVA16
                       organism = synthetic construct
SEQUENCE: 118
GCGGAAATGC GAGTTATTCA CCTACATGCG CTTTGATGCT GAATTTACAT TTGTCGTAGC  60
CAAACCCAAT GGTGAACTAG TCCCCCAATT ACTCCAATAC                        100

SEQ ID NO: 119         moltype = AA  length = 100
FEATURE                Location/Qualifiers
source                 1..100
                       mol_type = protein
                       note = enterovirus CVA16
                       organism = synthetic construct
SEQUENCE: 119
GCGGAAATGC GAGTTATTCA CCTACATGCG CTTTGATGCT GAATTCACAT TTGTCGTGGC  60
CAAACCCAAT GGTGAGTTGG TTCCCCAATT ACTGCAGTAC                        100

SEQ ID NO: 120         moltype = AA  length = 100
FEATURE                Location/Qualifiers
source                 1..100
                       mol_type = protein
                       note = enterovirus CVA16
                       organism = synthetic construct
SEQUENCE: 120
GCGGAAATGC GAGTTATTCA CCTACATGCG CTTTGATGCT GAATTCACAT TTGTCGTAGC  60
CAAACCCAAT GGTGAGCTAG TCCCCCAATT ACTCCAGTAC                        100

SEQ ID NO: 121         moltype = AA  length = 100
FEATURE                Location/Qualifiers
source                 1..100
                       mol_type = protein
                       note = enterovirus CVA16
                       organism = synthetic construct
SEQUENCE: 121
GCGGAAATGC GAGTTATTCA CCTACATGCG CTTTGATGCT GAATTCACAT TTGTCGTGGC  60
CAAACCCAAT GGTGAGTTGG TCCCCCAATT ACTGCAGTAC                        100

SEQ ID NO: 122         moltype = AA  length = 100
FEATURE                Location/Qualifiers
source                 1..100
                       mol_type = protein
                       note = enterovirus CVA16
                       organism = synthetic construct
SEQUENCE: 122
GCGGAAGTGC GAGTTATTTA CCTACATGCG CTTTGATGCT GAATTCACAT TTGTCGTAGC  60
CAAACCCAAT GGTGAGTTGG TCCCCCAATT ACTGCAGTAC                        100

SEQ ID NO: 123         moltype = AA  length = 100
FEATURE                Location/Qualifiers
source                 1..100
                       mol_type = protein
                       note = enterovirus CVA16
                       organism = synthetic construct
SEQUENCE: 123
GCGGAAATGC GAGTTATTCA CCTACATGCG CTTTGATGCT GAATTCACAT TTGTCGTAGC  60
CAAGCCCAAT GGTGAGCTAG TCCCCCAATT ACTCCAGTAC                        100
```

RPA-PAND BASED ENTEROVIRUS TYPING DETECTION KIT AND DETECTION METHOD

REFERENCE TO SEQUENCE LISTING

The sequence listing is submitted as an XML file filed via EFS-Web, with a file name of "WHZG-USP1243885-Sequence_Listing.XML", a creation date of Mar. 28, 2025, and a size of 139,317 bytes. The sequence Listing filed via EFS-Web is a part of the specification and is incorporated in its entirety by reference herein.

TECHNICAL FIELD

The present disclosure belongs to the technical field of enterovirus detection, and particularly relates to an RPA-PAND based enterovirus typing detection kit and a detection method.

BACKGROUND

Enteroviruses, as the main pathogens causing the hand-foot-and-mouth disease (HFMD), can induce acute infectious diseases in infants and young children. Mainly characterized by fever, herpes on hands, feet and buttocks, and oral mucosal ulcers, HFMD is generally self-limiting, however, severe patients have complications such as myocarditis, pulmonary edema and meningitis, and even neurological complications to cause death. The enterovirus EV is a class of single-stranded positive-chain RNA viruses from the enterovirus genus of the Picornaviridae family, is of a symmetrical icosahedron and has a genome of about 7.5 kb. Both ends of the genome of the enterovirus are 5' and 3' untranslated regions (UTR), 2194 amino acids are encoded on a continuous opening read frame (ORF) in the middle, and the Poly (A) tail behind the 3' UTR region plays a crucial role in infection and replication of enterovirus single-stranded RNA. The single polyprotein translated by the genome RNA can be further hydrolyzed into three precursor proteins (P1, P2 and P3), where the P1 precursor protein can be degraded into four virus coat proteins (VP1, VP2, VP3 and VP4), and the P2 and P3 precursor proteins can be finally hydrolyzed into the component including 2A (specific proteolytic enzyme), 2B, 2C, 3A and VPg (5' end-binding protein), 3C (specific proteolytic enzyme) and 3D (RNA polymerase). The enterovirus is divided into four enteroviruses (A, B, C and D) according to molecular biology and genetic characteristics thereof. Except for EV71 and CVA16 main pathogens, the outbreak tend of HFMD caused by CVA6 and CVA10 pathogens in many parts of the world increases year by year, and the detection for enterovirus infections has become a key focus of health and safety. Even if the clinic symptoms of HFMD are similar to these of the enteroviruses, infectious symptoms induced by different serotypes have specific manifestations, and people lack a cross-protection force for different types of enteroviruses, thus leading to a relatively high recurrent and incidence rate. At present, there are no drug intervenes or vaccines for HFMD caused by the rest main pathogens except that clinical trials for the development of the EV71 special vaccine have been completed. The coinfection of multiple EV pathogens and the evolution of molecular epidemiology make intervening measures only based on a single factor relatively insufficient. Therefore, the enhancement of the epidemic detection of enteroviruses to grasp its infection is of important significance for prevention and control of HFMD.

The clinic diagnosis standard for HFMD is mainly based on patient's epidemiological history, symptoms and various examinations, including blood routine examination, serological examination, pathogen examination, stool routine examination and endoscopic examination. The detection methods for the enteroviruses mainly include traditional virus isolation and cultivation, nucleic acid detection using reverse transcription-polymerase chain reaction (RT-PCR) and multiplex fluorescent RT-PCR, and enzyme linked immunosorbent assay (ELISA) serological detection based on antigen-binding antibodies. The traditional detection method is difficulty used for early diagnosis due to its complicated operation, long time and high requirements. The multiplex fluorescent RT-PCR cannot simultaneously detect three or more types of enteroviruses. With the establishment of a virus nucleic acid diagnostic method represented by a CRISPR/Cas system, the traditional clinical molecular diagnostic techniques have entered a new stage with low cost, high sensitivity and high specificity.

However, although the development of the CRISPR/Cas detection technology has reached the requirements of relatively high sensitivity and specificity, there are the problems of Cas effector protein off target, relatively high gRNA synthesis cost, PAM sequence dependence and limitations of multiplex detection complex systems. At present, novel diagnosis methods based on an endonuclease Argonaute protein have also been established successively, to achieve specific cleavage of DNA or RNA under the guidance of gDNA, however it has not yet reported that the enterovirus typing detection is performed using the endonuclease Argonaute protein.

SUMMARY

In view of this, the present disclosure aims to establish an RPA-HFMD-PAND quick nucleic acid detection system for typing detection of common enterovirus type A pathogens EV71, CVA6, CVA10, CVA16, and enterovirus universal EVU by utilizing a PfAgo-mediated nucleic acid detection (PAND) technology in combination with a recombinant enzyme polymerase amplification (RPA) technology.

The technical solution of the present disclosure is specifically as follows:

A first aspect of the present disclosure provides an enterovirus typing detection kit, comprising a PfAgo protein, and gDNA (guide DNA) and a molecular beacon (MB) for specifically detecting enteroviruses EV71, CVA6, CVA10, CVA16 and universal EVU typing, which is specifically as follows:

- gDNA and MB for specifically detecting enterovirus universal EVU, where MB-EVU is as shown in SEQ ID NO.2, and EVU-g1, EVU-g2 and EVU-g3 are as shown in SEQ ID NO.3-5, respectively;
- gDNA and MB for specifically detecting enterovirus universal EV71, where MB-EV71 is as shown in SEQ ID NO.7, and EV71-g1, EV71-g2 and EV71-g3 are as shown in SEQ ID NO.8-10, respectively;
- gDNA and MB for specifically detecting enterovirus CVA6, where MB-CVA6 is as shown in SEQ ID NO.12, and CVA6-g1, CVA6-g2 and CVA6-g3 are as shown in SEQ ID NO.13-15, respectively;
- gDNA and MB for specifically detecting enterovirus CVA10, where MB-CVA10 is as shown in SEQ ID NO.17, and CVA10-g1, CVA10-g2 and CVA10-g3 are as shown in SEQ ID NO.18-20, respectively; and gDNA and MB for specifically detecting enterovirus CVA16, where MB-CVA16 is as shown in SEQ ID NO.22, and CVA16-g1, CVA16-g2 and CVA16-g3 are as shown in SEQ ID NO.23-25, respectively.

In the above-mentioned enterovirus typing detection kit, the gDNA and MB combinations for different enteroviruses can be used separately or in combination. When used in combination, the gDNA and MB combination can achieve the simultaneous detection of multiple enteroviruses, with detection cost saved, but also has good specificity.

Preferably, in the above-mentioned enterovirus typing detection kit, MB carries a fluorophore which is selected from FAM, CY5, TET, ROX and HEX, etc. For example, in an embodiment of the present disclosure, MB-EVU carries fluorophore CY5, MB-EV71 carries fluorophore FAM, MB-CVA6 carries fluorophore TET, MB-CVA10 carries fluorophore ROX, and MB-CVA16 carries fluorophore HEX.

Preferably, the above-mentioned enterovirus typing detection kit comprises the following RPA primers:

EVU-RPA-F/R with sequences as shown in SEQ ID NO.26 and SEQ ID NO.27;

EV71-RPA-F/R with sequences as shown in SEQ ID NO.28 and SEQ ID NO.29;

CVA6-RPA-F/R with sequences as shown in SEQ ID NO.30 and SEQ ID NO.31;

CVA10-RPA-F/R with sequences as shown in SEQ ID NO.32 and SEQ ID NO.33; and

CVA16-RPA-F/R with sequences as shown in SEQ ID NO.34 and SEQ ID NO.35.

The recombinant enzyme polymerase amplification (RPA) technology has the advantages of simple operation, low instrument requirements and quick field detection. The introduction of the RPA primers in the detection kit of the present disclosure not only can significantly improve the detection sensitivity, but also is more beneficial for shortening the detection time relative to conventional PCR.

Preferably, in the above-mentioned enterovirus typing detection kit, the PfAgo protein is a recombinant protein carrying a His tab, with an amino acid sequence as shown in SEQ ID NO.36.

A second aspect of the present disclosure provides a PAND-based enterovirus typing detection method, comprising the following steps:

S1, extracting DNA of a to-be-detected sample;

S2, constructing a PAND detection system containing the PfAgo protein, gDNA and MB by using the DNA sample obtained in S1 as a detection object for reaction;

the gDNA and MB comprising at least one of the following 5 combinations:

a gDNA and MB combination for specifically detection of enterovirus universal EVU, with sequences as shown in SEQ ID NO.2-5;

a gDNA and MB combination for specifically detection of enterovirus EV71, with sequences as shown in SEQ ID NO.7-10;

a gDNA and MB combination for specifically detection of enterovirus CVA6, with sequences as shown in SEQ ID NO.12-15;

a gDNA and MB combination for specifically detection of enterovirus CVA10, with sequences as shown in SEQ ID NO.17-20; and a gDNA and MB combination for specifically detection of enterovirus CVA16, with sequences as shown in SEQ ID NO.22-25.

Preferably, in the above-mentioned enterovirus typing detection method, the step S1 specifically comprises: extracting DNA of a to-be-detected sample, amplifying through RPA primers using the obtained DNA as a template to obtain an RPA product; where the RPA product comprises a target region for gDNA and MB detection. Therefore, an enterovirus typing detection method based on an RPA technology combined with PAND is constructed, which is marked as an RPA-PAND method.

More preferably, in the above-mentioned RPA-PAND method, the RPA primers are selected from at least one pair of the following primer pairs:

EVU-RPA-F/R with sequences as shown in SEQ ID NO.26 and SEQ ID NO.27;

EV71-RPA-F/R with sequences as shown in SEQ ID NO.28 and SEQ ID NO.29;

CVA6-RPA-F/R with sequences as shown in SEQ ID NO.30 and SEQ ID NO.31;

CVA10-RPA-F/R with sequences as shown in SEQ ID NO.32 and SEQ ID NO.33; and

CVA16-RPA-F/R with sequences as shown in SEQ ID NO.34 and SEQ ID NO.35.

It is noted that, for the same conserved sequence of a certain enterovirus, multiple pairs of RPA primers can be designed, but amplification products have relatively large effects on the intensity of a fluorescence signal detected by a PAND detection system.

More preferably, in the above-mentioned RPA-PAND method, the conditions for amplification through the RPA primers are as follows: react for 10-20 min at 37° C.

Preferably, in the above-mentioned enterovirus typing detection method, the condition for reaction in the step S2 is as follows: react for 30 min at 95° C.

Preferably, in the above-mentioned enterovirus typing detection method, the MB carries a fluorophore, and the type of the enterovirus in the to-be-detected sample is determined according to different fluorophores carried by the MBs of different enteroviruses.

Compared with the prior art, the present disclosure has the beneficial effects:

(1) High social value. In the present disclosure, the RPA-HFMD-PAND quick nucleic acid detection methods (including HFMD-PAND and RPA-HFMD-PAND) for typing detection of common enterovirus type A pathogens EV71, CVA6, CVA10, CVA16 and enterovirus universal EVU are successfully established for the first time based on PfAgo protein mediated target detection. The method has the advantages of speediness, high sensitivity, high specificity, low cost, low position targeting restriction, simple reaction system and no aerosol pollution, can conduct multi-channel nucleic acid detection, deals with complicated samples, and is suitable for clinical application.

(2) Strong core competitiveness. Relative to clinical HFMD diagnosis standard, traditional virus isolation and culture, RT-PCR/qRT-PCR nucleic acid detection and serological detection, the present disclosure is an ideal pathogen detection method, and meets the requirements of POCT (Point-of-Care Testing, i.e., quick, sensitive, specific, low equipment requirements, and cost-effective); in addition, the lower limit of enterovirus related genes detected by using a Cas12a system detection platform based on multiplex nucleic acid amplification (MARPLES) developed by using the existing technology in 1 h reaches 1 copy/μL, however, the RPA-HFMD-PAND method of the present disclosure has a detection lower limit of 0.01-1 copy/μL, with a higher target screening freedom degree.

(3) Good potential benefits. Compared with the conventional virus detection technology and equipment, the present disclosure can save labor cost and solvent cost; it has been proved that the present disclosure can purify over 100 nmol of PfAgo from each liter of culture medium, recombinase polymerase amplification and PAND detection can only be conducted under two temperature conditions (where 37° C. and 95° C. are preferred), thereby significantly reducing the requirements on equipment and personnel operation.

DETAILED DESCRIPTION OF THE EMBODIMENTS

Next, the technical solution of the present disclosure will be described in detail in combination with drawings and embodiments. The following embodiments are only for more clearly illustrating the technical solution of the present disclosure, but not limiting the scope of protection of the present disclosure.

Unless otherwise defined, all technical and scientific terms used in the present disclosure have the same meaning as those commonly understood by those skilled in the art; the terms "comprise" and other any deformations in the specification and claims of the present disclosure are intended to cover non-exclusive inclusions.

The enterovirus is a main pathogen causing HFMD, which can induce acute infectious diseases in infants and young children, and severe patients have complications such as myocarditis, pulmonary edema, meningitis, and even neurological diseases that can cause death. People lack the cross-protection force of different types of enteroviruses, with high recurrent incidence rate. As the trend HFMD outbreaks in many parts of the world increases year by year, and therefore the detection of enterovirus infection has become a key focus of health and safety.

To achieve the quick identification of different types of enteroviruses, an RPA-HFMD-PAND quick nucleic acid detection method for typing detection of common enterovirus type A pathogens EV71, CVA6, CVA10, CVA16 and enterovirus universal EVU is successfully established based on PfAgo protein mediated target detection in combination with an RPA technology. The method at least involves the following reagents:

a PfAgo protein;

a gDNA and MB combination for specifically detection of enteroviruses EV71, CVA6, CVA10, CVA16 and universal EVU;

an RPA primer for specifically detection of enteroviruses EV71-2A, CVA6-VP1, CVA10-VP1, CVA16-VP1 and universal EVU.

Figure 1:
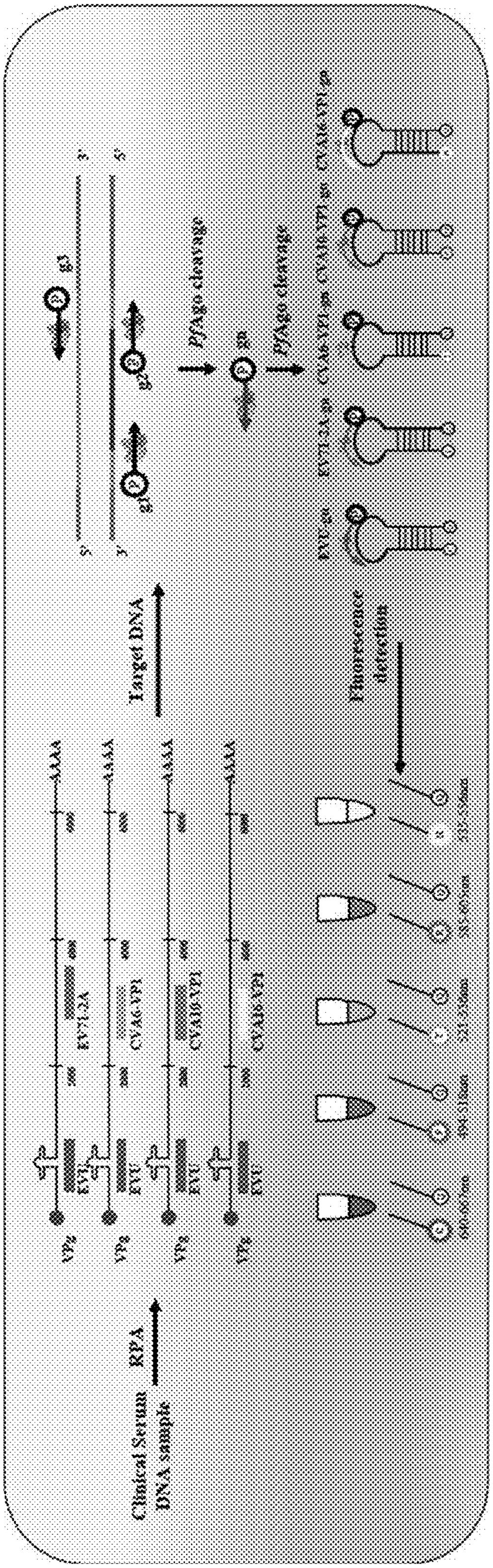
FIG. 1 is a diagram of an RPA-PAND based enterovirus typing detection method established according to the present disclosure.

The working principle of the method is as shown in FIG. 1. The method specifically comprises the following procedures:

(1) extracting DNA of a to-be-detected sample (such as a clinical serum sample);

(2) amplifying DNA extracted in step (1) by utilizing the RPA primer to obtain an RPA amplification product (i.e., Target DNA in FIG. 1); and (3) constructing a PAND detection system containing the RPA amplification product, the PfAgo protein, gDNA and MB for reaction; when the MB carries a fluorophore, whether the to-be-detected sample contains enteroviruses and their types is determined directly by collected fluorescence signals.

If no specific technology or conditions are specified in the following embodiments, they shall be carried out according to the technology or conditions described in the literature in this field or according to the product manual; the reagents or instruments used without specifying the manufacturer are conventional products that can be obtained through commercial purchase.

Example 1

This example provides a PAND kit for enterovirus typing detection, comprising a PfAgo protein, and gDNA and MB for detecting enteroviruses EV71, CVA6, CVA10, CVA16 and universal EVU. The acquisition and verification of the above-mentioned protein, gDNA and MB comprises the following steps:

(1) Preparation of PfAgo Protein

A pET-23a-PfAgo recombinant plasmid was constructed, and then the constructed pET-23a-PfAgo recombinant plasmid was transformed into an *E. coli*BL21 (DE3) strain. After induced expression for 16 h under the conditions of 0.5 mM IPTG and 18° C., bacterial precipitates were collected, and then subjected to resuspension and ultrasonic bacteria breakage using PfAgo lysis buffer (20 mM Tris-HCl, 200 mM NaCl, and 0.2 mM $MnCl_2$) to break bacteria. After centrifuging for 10 min at 12000 rpm, the supernatant of the broken bacteria was taken and heteroproteins in the supernatant were removed at 70° C., and then the supernatant without heteroproteins was combined with nickel column Ni-NTA for incubation, and subsequently the protein solution after incubation was subjected to gradient elution using PfAgo lysis buffer containing different imidazole concentrations. The protein solution containing 50-300 mM of imidazole was concentrated by ultrafiltration, and changed into PfAgo Elution buffer (20 mM Tris-HCl, 300 mM NaCl, and 0.5 mM $MnCl_2$), and finally 10% SDS-PAGE gel electrophoresis results were verified.

Figure 2:
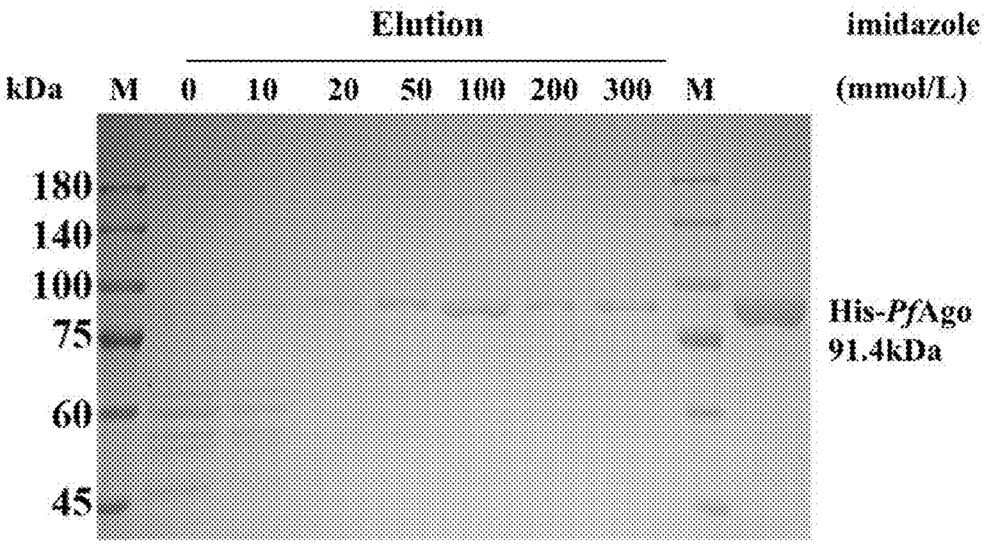
FIG. 2 is a diagram showing prokaryotic expression and purification results of a His-PfAgo fusion protein in example 1.

The SDS-PAGE map as shown in FIG. 2 shows the prokaryotic expression and purification results of the PfAgo protein. The eluted protein solution containing 50-300 mM of imidazole was collected, in which the size of the protein was consistent with an expected protein size of 91.4 kDa. After ultrafiltration concentration and solution exchange, the concentration of the protein was measured as 1.875 mg/ml. The amino acid sequence of the recombinant protein (i.e., His-PfAgo fusion protein) prepared in this example is as shown in SEQ ID NO.36.

(2) Identification of Endonuclease Activity of PfAgo Protein

Figure 3:
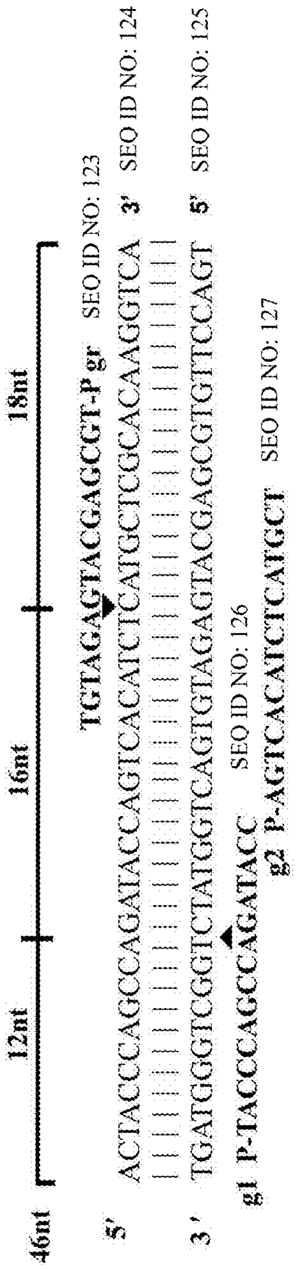
FIG. 3 is a diagram showing a mechanism for identifying endonuclease activity of a His-PfAgo fusion protein in example 1.

Two complementary sequences containing target gene fragments, three strands of gDNA targeting target gene sites and corresponding molecular beacons MB were designed (specifically as shown in FIG. 3). The phosphorylated gDNA was added into the detection system (a molar ratio of gDNA to PfAgo was 1:10) to react for 30 min at 95° C. A sample was added into 2×TBE-PAGE Loading to be incubated for 5 min at 95° C., and then subjected to 20% TBE-PAGE electrophoresis. The product after electrophoresis was stained for 5 min using SYBR Gold nucleic acid dye in the dark to verify digestion results.

Figure 4:
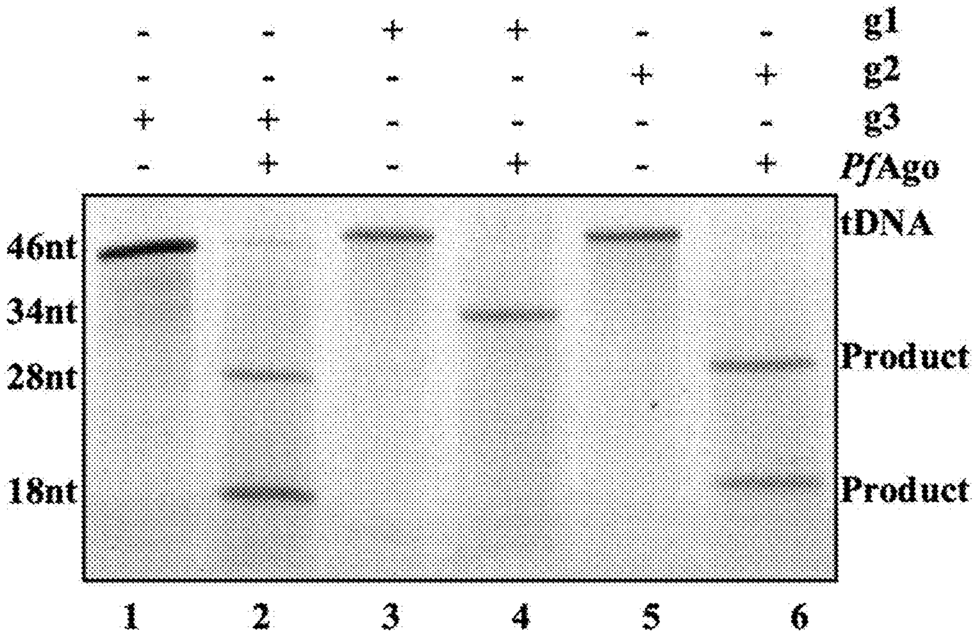
FIG. 4 is a diagram showing results for identifying endonuclease activity of a His-PfAgo fusion protein in example 1. In the figure, lanes 1, 3, 5 only contain single-stranded DNA targets, lanes 2, 4, 6 contain gDNA and PfAgo.

The TBE-PAGE map as shown in FIG. 4 shows the size of single-stranded DNA is 46 nt, which is the size of a corresponding cleavage product after PfAgo enzyme digestion reaction. The gDNA-g3 cleavage products are 18 nt and 28 nt in size, the gDNA-g1 cleavage products are 12 nt and 34 nt in size, and the gDNA-g2 cleavage products are 18 nt and 28 nt in size, which are consistent with expected cleavage results. This indicates that the purified His-PfAgo fusion protein has the activity of cleaving DNA from the 10th position to 11th position of the 5' end under the action of phosphorylated gDNA.

(3) Multiplex Sequence Alignment Analysis of Enterovirus Gene and Screening of gDNA and MB According to the gene sequences of enteroviruses EV71, CVA16, CVA6, CVA10 provided by GeneBank, multiplex sequence alignment was conducted in MEGA11 for phylogenetic analysis. Based on the phylogenetic analysis, multiplex sequence alignment was performed on enteroviruses EV71, CVA6, CVA10, CVA16 and enterovirus universal EVU, and finally the 2A sequence (EV71-2A) in EV71 and VP1 sequences (CVA6-VP1, CVA10-VP1, and CVA16-VP1) in CVA6, CVA10 and CVA16 were selected as conserved regions of gDNA and MB. Positive plasmids of various viruses were constructed according to the conserved regions, which were marked as EVU P, EV71-2A P, CVA6-VP1 P, CVA10-VP1 P and CVA16-VP1 P, respectively.

Figure 5A:
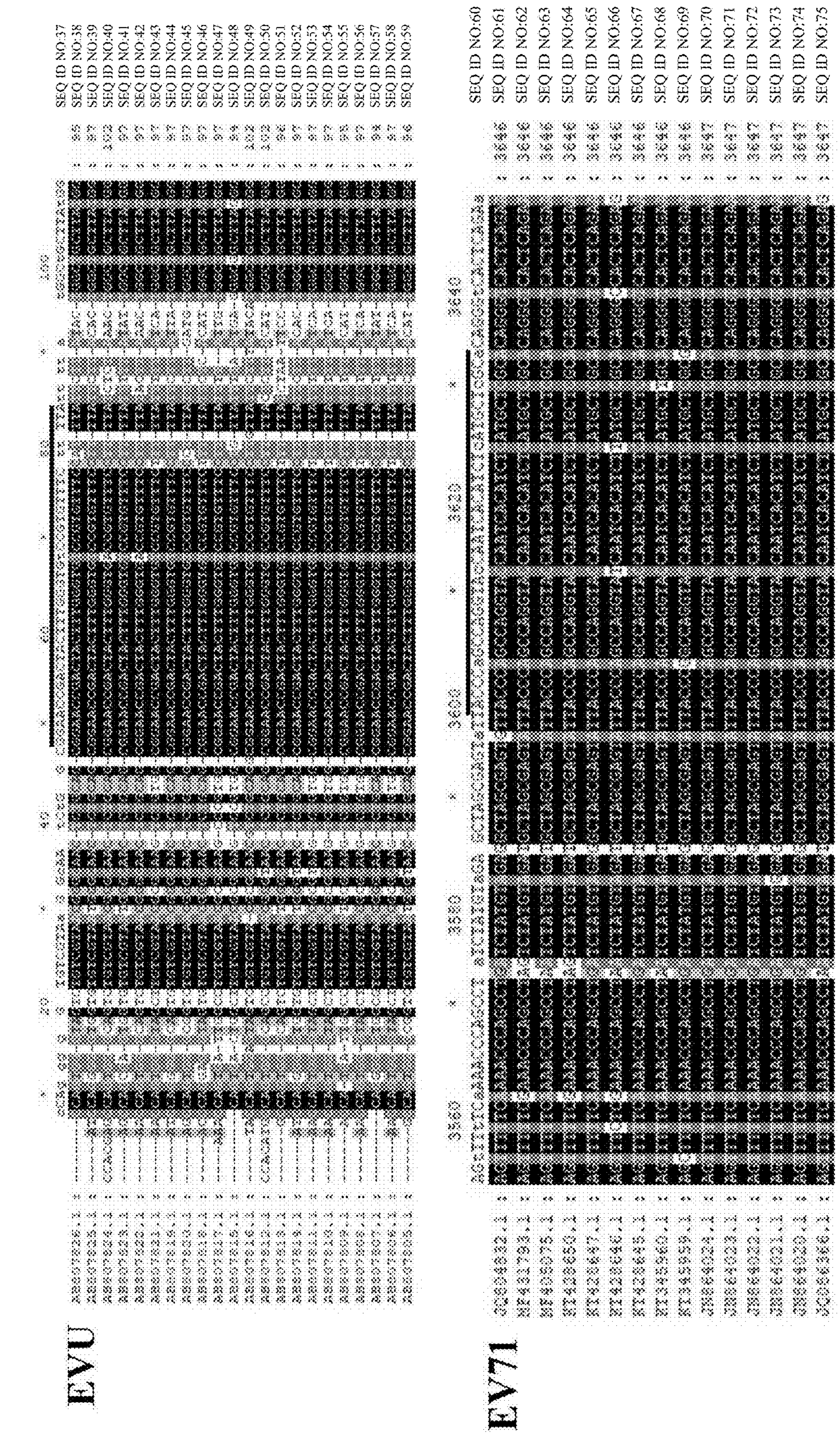
FIG. 5A, FIG. 5B and FIG. 5C show a region of finally screened gDNA and MB in example 1.
Figure 5B:
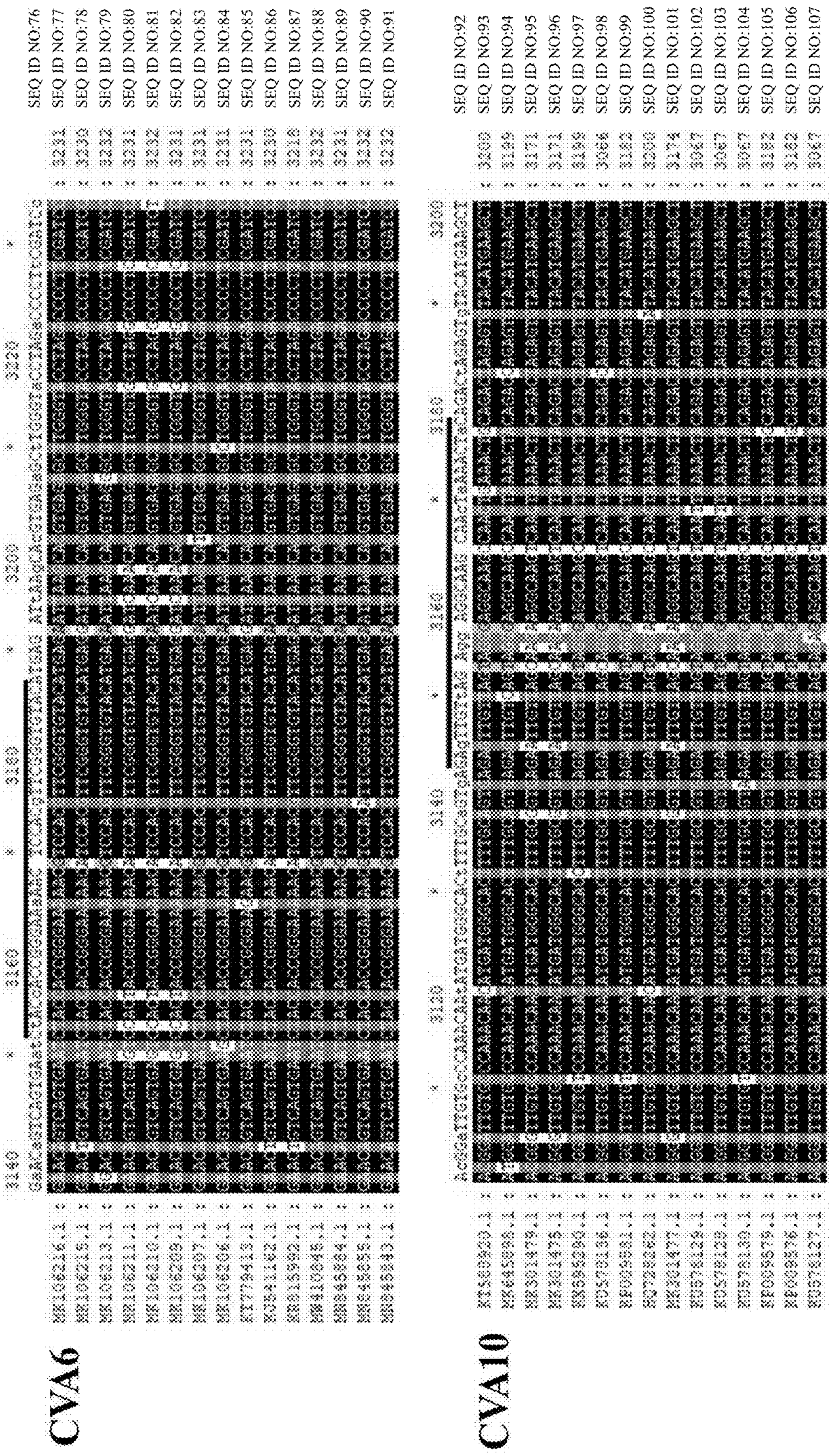
Figure 5C:
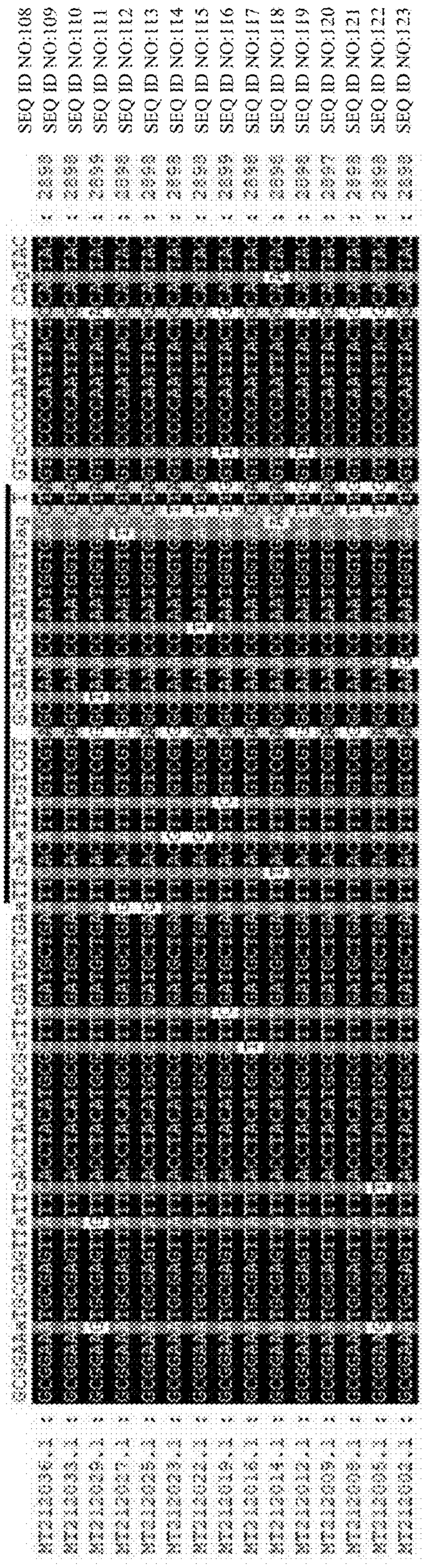
Figure 6A:
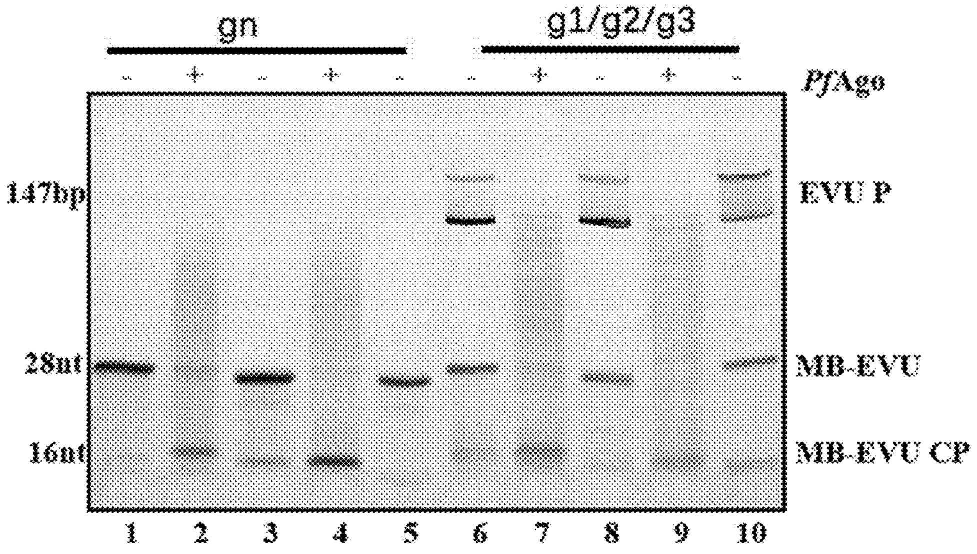
FIG. 6(*a*), FIG. 6(*b*), FIG. 6(*c*), FIG. 6(*d*) and FIG. 6(*e*) are Tris boric acid (TBE)-polyacrylamide gel electrophoresis (PAGE) maps showing conserved sequence screening of different enteroviruses, where a) is a TBE-PAGE map showing conserved sequence screening of enterovirus universal EVU; b) is a TBE-PAGE map showing conserved sequence screening of enteroviruses EV71-2A; c) is a TBE-PAGE map showing conserved sequence screening of enterovirus CVA6-VP1; d) is a TBE-PAGE map showing conserved sequence screening of enterovirus CVA10-VP1; e) is a TBE-PAGE map showing conserved sequence screening of enterovirus CVA16-VP1; where lanes 1-5 in each map show screening of gn and molecular beacon MB, and lanes 6-10 in each group show the screening of three strands of gDNA.
Figure 6B:
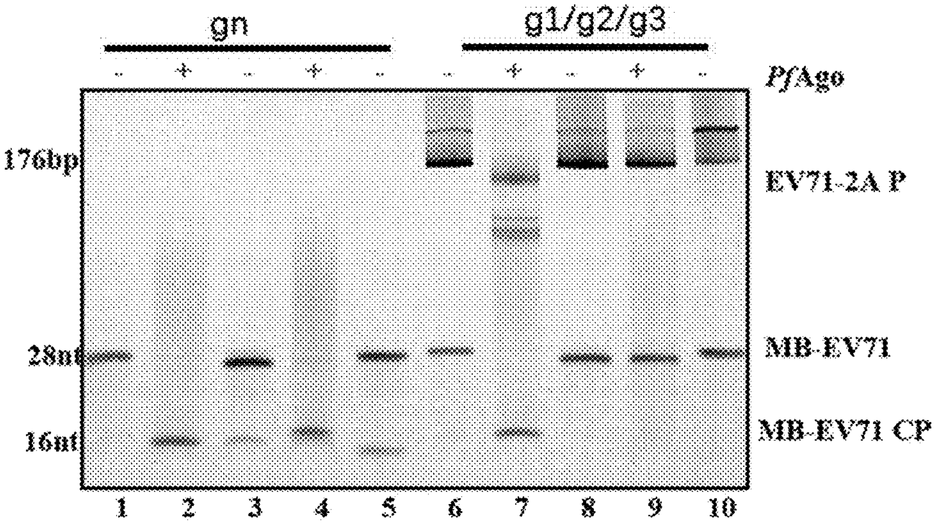
Figure 6C:
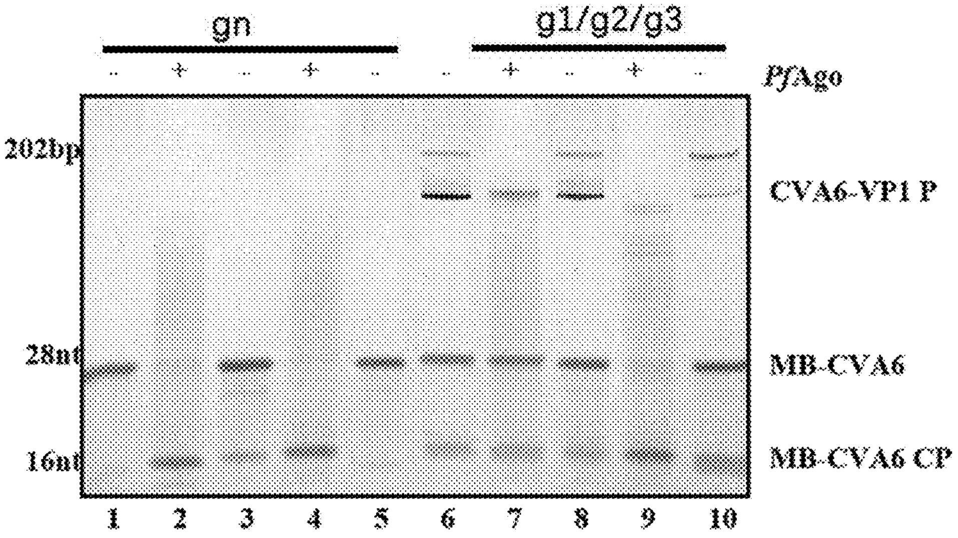
Figure 6D:
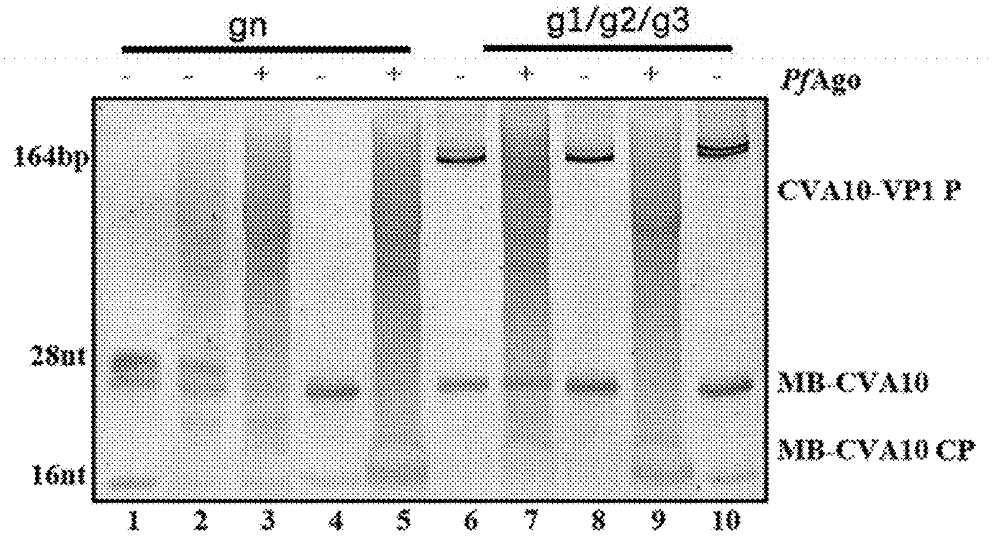
Figure 6E:
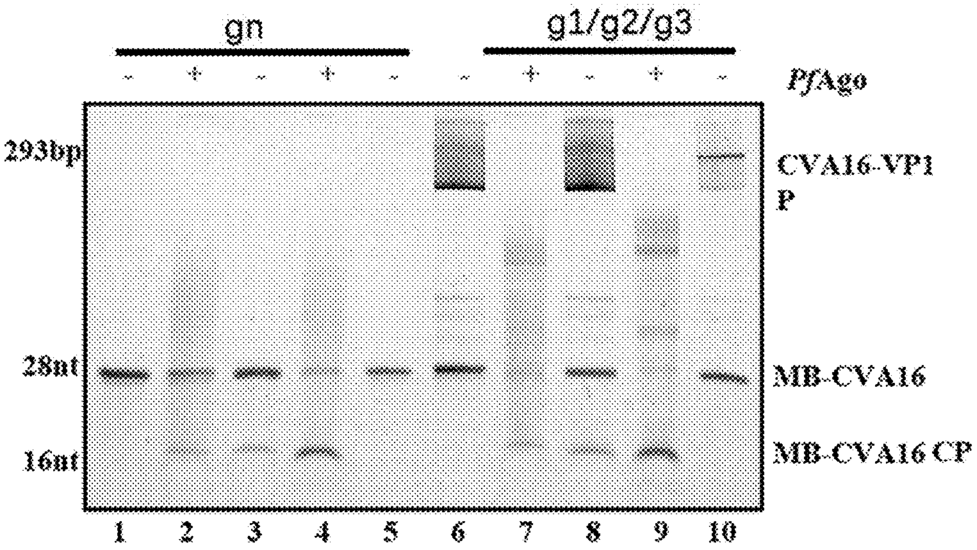
Figure 7A:
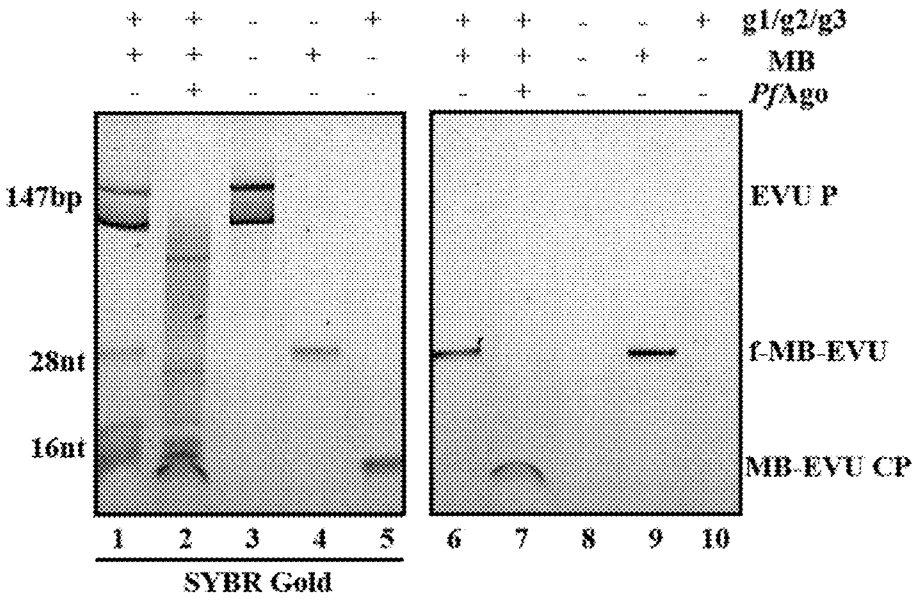
FIG. 7(*a*), FIG. 7(*b*), FIG. 7(*c*), FIG. 7(*d*) and FIG. 7(*e*) are TBE-PAGE maps showing the detection of different enteroviruses utilizing a PAND method in example 1; where a) is a TBE-PAGE map showing the detection of enterovirus universal EVU utilizing a PAND method; b) is a TBE-PAGE map showing the detection of enterovirus EV71-2A utilizing a PAND method; c) is a TBE-PAGE map showing the detection of enterovirus CVA6-VP1 utilizing a PAND method; d) is a TBE-PAGE map showing the detection of enterovirus CVA10-VP1 utilizing a PAND method; e) is a TBE-PAGE map showing the detection of enterovirus CVA16-VP1 utilizing a PAND method, where lane 1 in each group contains a target gene, gDNA and molecular beacon f-MB, lane 2 in each group contains a target gene, gDNA and molecular beacon f-MB, and a His-PfAgo protein that is added, lanes 3-5 in each group are negative controls in which components in the reaction system are only added, and lanes 6-10 in each group only show the cleavage of molecule beacon f-MB.
Figure 7B:
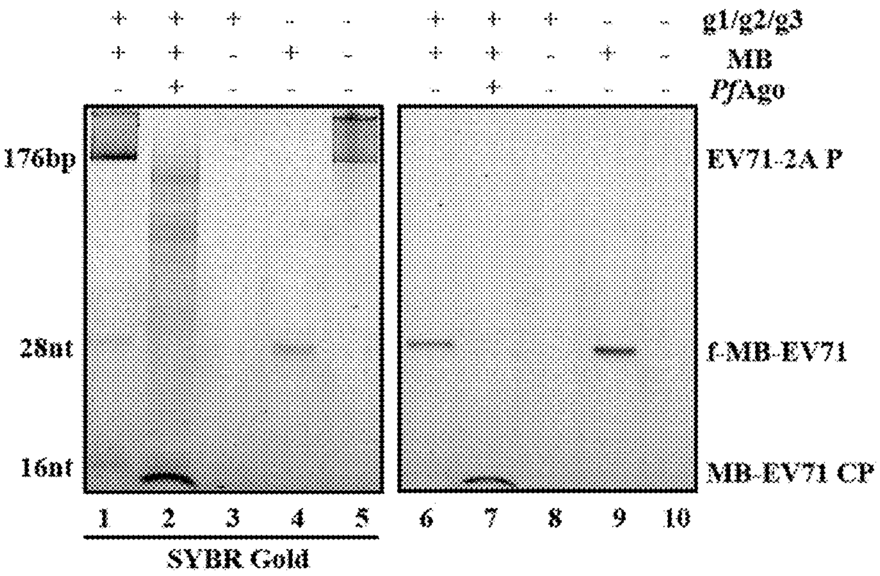
Figure 7C:
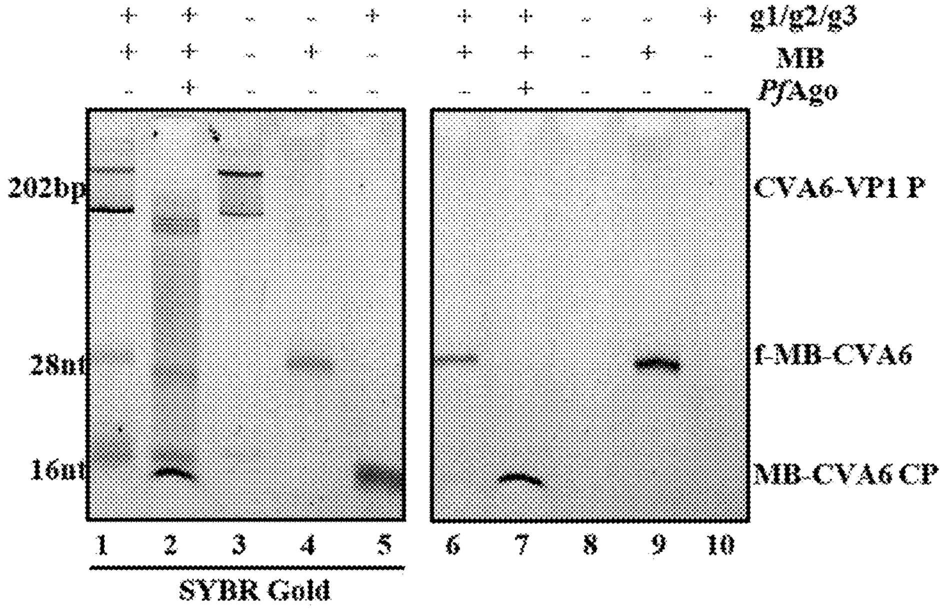
Figure 7D:
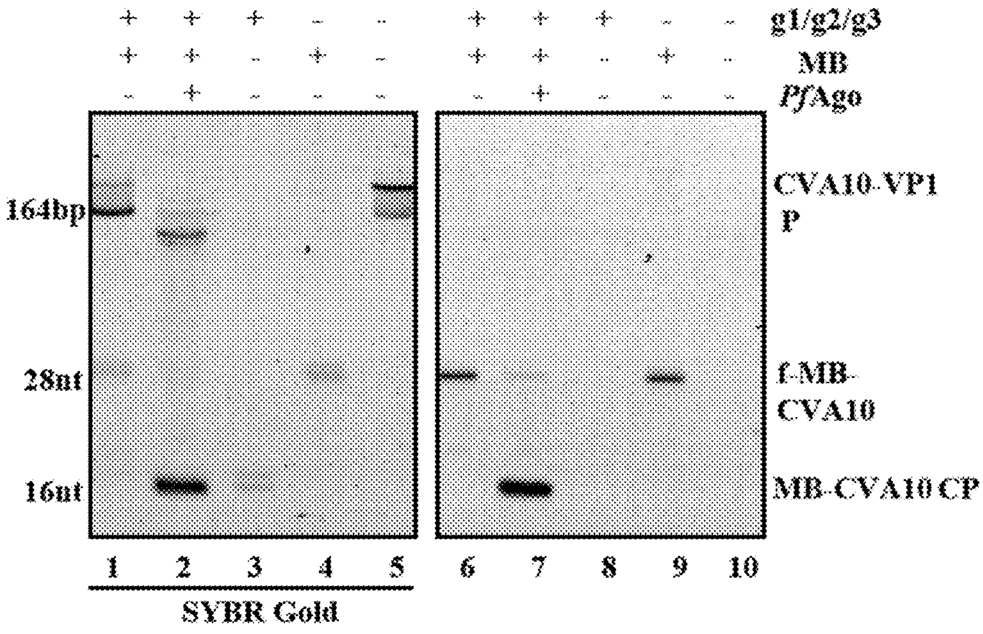
Figure 7E:
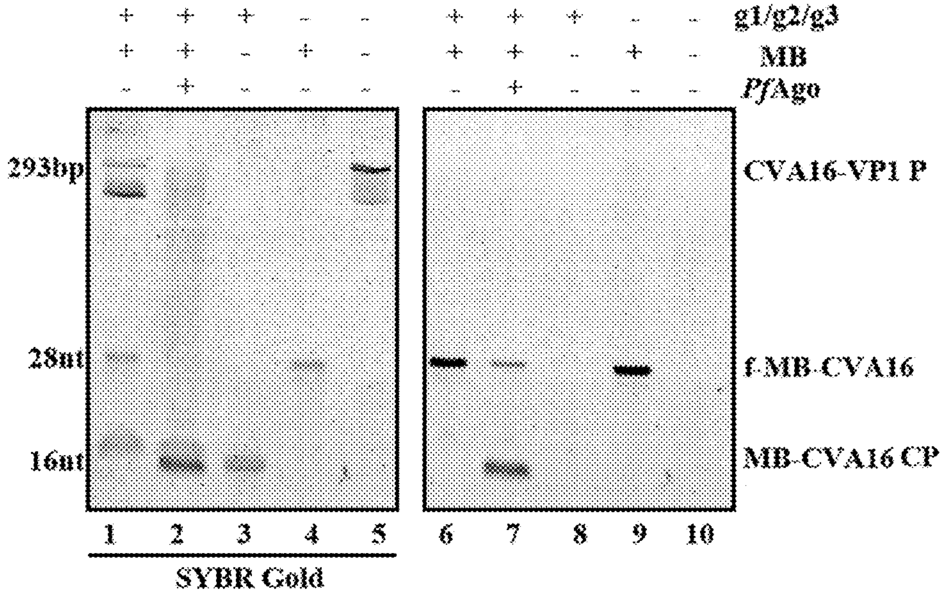

The specific fragment of each enterovirus type in the conserved region was screened and corresponding gDNA and MB were designed, and then screening and TBE-PAGE electrophoresis verification were conducted through a PfAgo enzyme digestion detection system (in which a system for gDNA phosphorylation is as shown in Table 1, and an enzyme digestion screening system is as shown in Table 2). Finally, 5 groups of gDNA and MB corresponding to different sequence targets were obtained, specifically as shown in Table 3. Furthermore, the regions of the obtained gDNA and MB are screened, which are specifically as shown in FIG. 5A, FIG. 5B and FIG. 5C, and the screened TBE-PAGE results are as shown in FIG. 6(*a*), FIG. 6(*b*), FIG. 6(*c*), FIG. 6(*d*) and FIG. 6(*e*).

TABLE 1

Reaction system of phosphorylated gDNA

| Component | Volume |
|---|---|
| DEPC | 6.8 μL |
| T4 PNK (10 U/μL) | 0.2 μL |
| gDNA (100 pmol/μL) | 1 μL |
| 10 mM ATP | 1 μL |
| 10xT4 PNK buffer | 1 μL |

TABLE 2

PfAgo-mediated screening system

| Component | Volume |
|---|---|
| His-pfAgo protein (10 pmol/μL) | 2 μL |
| gDNA (2 pmol/μL) | 1 μL |
| PfAgo reaction buffer (10x) | 1 μL |
| $ddH_2O$ | 5.5 μL |
| MB (10 pmol/μL) | 0.5 μL |

TABLE 3

Information of gDNA and MB obtained by screening

| Entero-virus | gDNAorMB | Sequence (5'-3') | Sequennumberce |
|---|---|---|---|
| EVU | gMB-EVU | cacggacacccaaagt | SEQ ID NO. 1 |
| | MB-EVU | actttgggtgtccgtg | SEQ ID NO. 2 |
| | EVU-g1 | ggaaccgactactttg | SEQ ID NO. 3 |
| | EVU-g2 | ggtgtccgtgtttcct | SEQ ID NO. 4 |
| | EVU-g3 | taaaaggaaacacgga | SEQ ID NO. 5 |
| EV71 | gMB-EV71 | agatgtgactggtatc | SEQ ID NO. 6 |
| | MB-EV71 | gataccagtcacatct | SEQ ID NO. 7 |
| | EV71-g1 | tacccagccagatacc | SEQ ID NO. 8 |
| | EV71-g2 | agtcacatctcatgct | SEQ ID NO. 9 |
| | EV71-g3 | tgcgagcatgagatgt | SEQ ID NO. 10 |
| CVA6 | gMB-CVA6 | aacgtggacgtttttc | SEQ ID NO. 11 |
| | MB-CVA6 | gaaaaacgtccacgtt | SEQ ID NO. 12 |
| | CVA6-g1 | ctaccaccgggaaaaa | SEQ ID NO. 13 |
| | CVA6-g2 | cgtccacgttcgggtg | SEQ ID NO. 14 |
| | CVA6-g3 | tgtacacccgaacgtg | SEQ ID NO. 15 |
| CVA10 | gMB-CVA10 | ttggcttgccttccta | SEQ ID NO. 16 |
| | MB-CVA10 | taggaaggcaagccaa | SEQ ID NO. 17 |
| | CVA10-g1 | gagttgtcagtaggaa | SEQ ID NO. 18 |
| | CVA10-g2 | ggcaagccaactaaaa | SEQ ID NO. 19 |
| | CVA10-g3 | gtagttttagttggct | SEQ ID NO. 20 |
| CVA16 | gMB-CVA16 | ttgggcttggctacga | SEQ ID NO. 21 |
| | MB-CVA16 | tcgtagccaagcccaa | SEQ ID NO. 22 |
| | CVA16-g1 | ttcacgtttgtcgtag | SEQ ID NO. 23 |
| | CVA16-g2 | ccaagcccaatggtga | SEQ ID NO. 24 |
| | CVA16-g3 | tagctcaccattgggc | SEQ ID NO. 25 |

(4) Establishment of PfAgo-Mediated Targeted Enterovirus Typing Detection System Using Screened gDNA and MB According to the MB screened in step (3), a molecular beacon (i.e., MB) carrying an FAM fluorophore was synthesized, and a PAND detection system was constructed (Table 2). After 20% TBE-PAGE electrophoresis, it was verified by adhesive irradiation that FAM-MB of 28 nt was cleaved into a beacon product of 16 nt by a PfAgo enzyme in a wavelength range of 495-518 nm. After staining with SYBR Gold nucleic acid dye for 5 min in the dark, it is verified that the amplification products of different enteroviruses changed under the activity cleavage of PfAgo.

The detection results are as shown in FIG. 7(*a*), FIG. 7(*b*), FIG. 7(*c*), FIG. 7(*d*) and FIG. 7(*e*), proving that the screened gDNA and MB can be used for establishing the PfAgo-mediated targeted enterovirus typing detection system.

Example 2

This example provides an RPA-PAND kit for enterovirus typing detection, comprising RPA primers for different enteroviruses except the PfAgo protein, gDNA and MB in example 1, specifically as shown in Table 4.

TABLE 4

RPA primer information of different enteroviruses

| Entero-virus | RPA primer | Sequence (5'-3') | Sequence number |
|---|---|---|---|
| EVU | EVU-1-F | CCACATGCCAGTGGGCAGCCTGTCGTAACGG | SEQ ID NO. 26 |
| | EVU-RAU-3-R | GATGGCCAATCCAATAGCGAGATGGCAACAA | SEQ ID NO. 27 |
| EV71 | EV71-RAA-3-F | GCCAGACAGGGGTGTATTATTGTAATTCAAGG | SEQ ID NO. 28 |
| | EV71-RAA-3-R | GCATCTAAGGATACCGCCACAATCACCAGG | SEQ ID NO. 29 |
| CVA6 | CVA6-RA6-2-F | GCCACTTTGCCATCCGAACAGTCAGTGAAT | SEQ ID NO. 30 |
| | CVA6-RA6-3-R | TAATCCGTGGTGGTTATGCTTGCACGGTCGG | SEQ ID NO. 31 |
| CVA10 | CVA10-4-F | ACTTTCGGCCAGCACCCGGAGACCTCAAACACAAC | SEQ ID NO. 32 |
| | CVA10-RA10-2-R | CTCGGGACCCAGGCCCTCACATGCTTAA | SEQ ID NO. 33 |
| CVA16 | CVA16-RA16-2-F | ACTCTACACAGGAGACAGCCATTGGGAA | SEQ ID NO. 34 |
| | CVA16-RA16-3-R | GGTGGCGCAAGCAAACGAATCTCTGGAAGT | SEQ ID NO. 35 |

Figure 8:
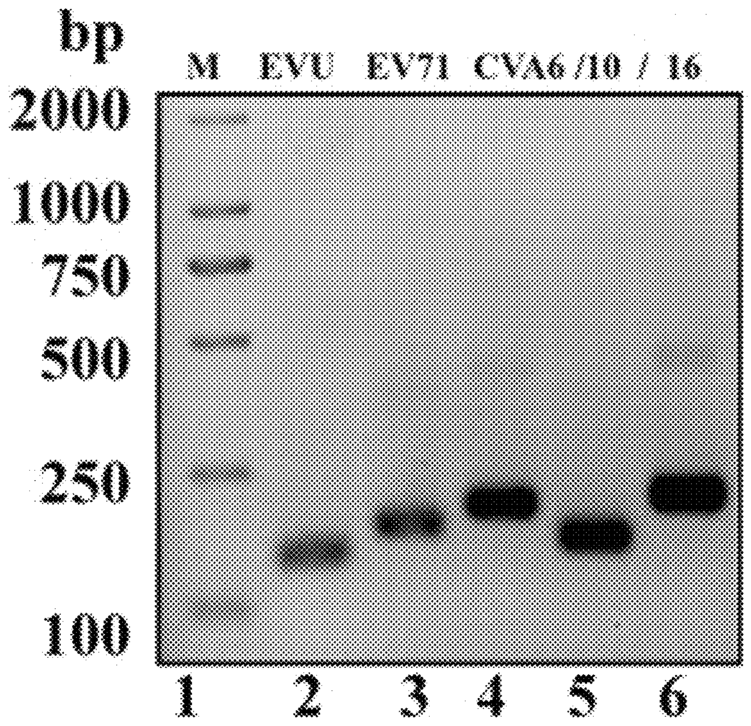
FIG. 8 shows agarose gel detection results of RPA primer amplification fragments of different enteroviruses in example 2; M: DL2000 DNA maker; 1: enterovirus universal EVU amplification fragment; 2: EV71-2A region amplification fragment; 3: CVA6-VP1 region amplification fragment; 4: CVA10-VP1 region amplification fragment; 5: CVA16-VP1 region amplification fragment.
Figure 9A:
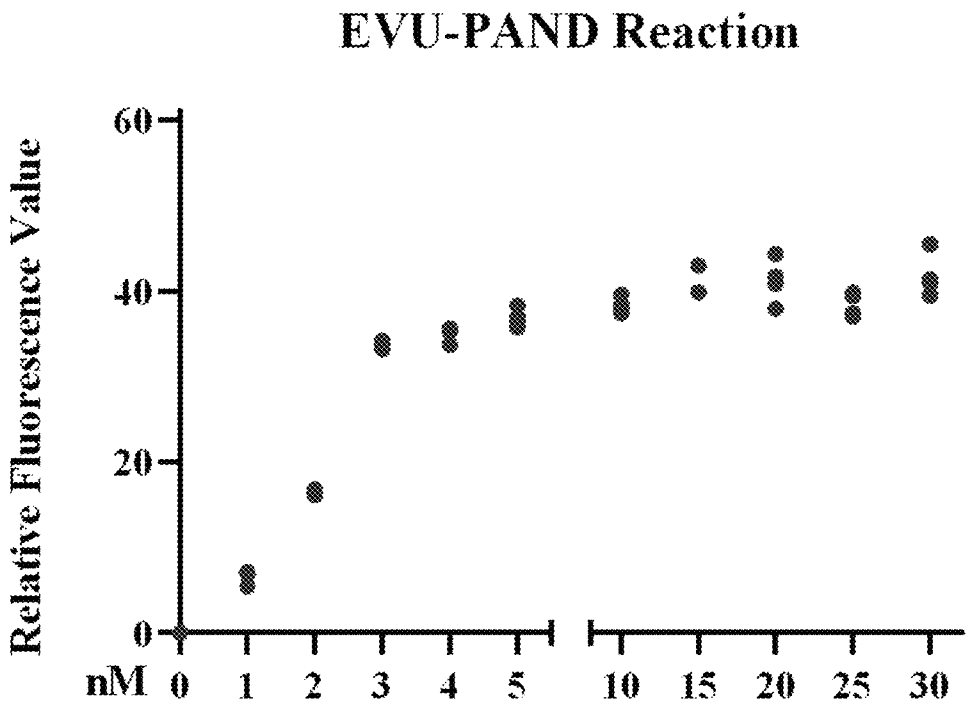
FIG. 9(*a*), FIG. 9(*b*), FIG. 9(*c*), FIG. 9(*d*) and FIG. 9(*e*) show sensitivity test results of a PAND method according to the present disclosure.
Figure 9B:
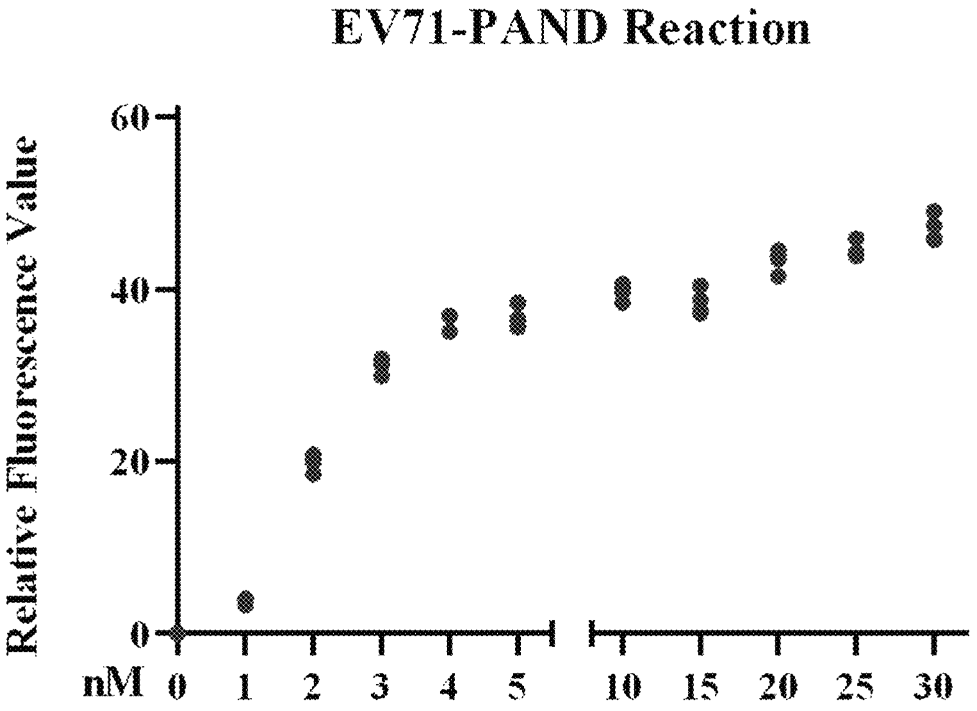
Figure 9C:
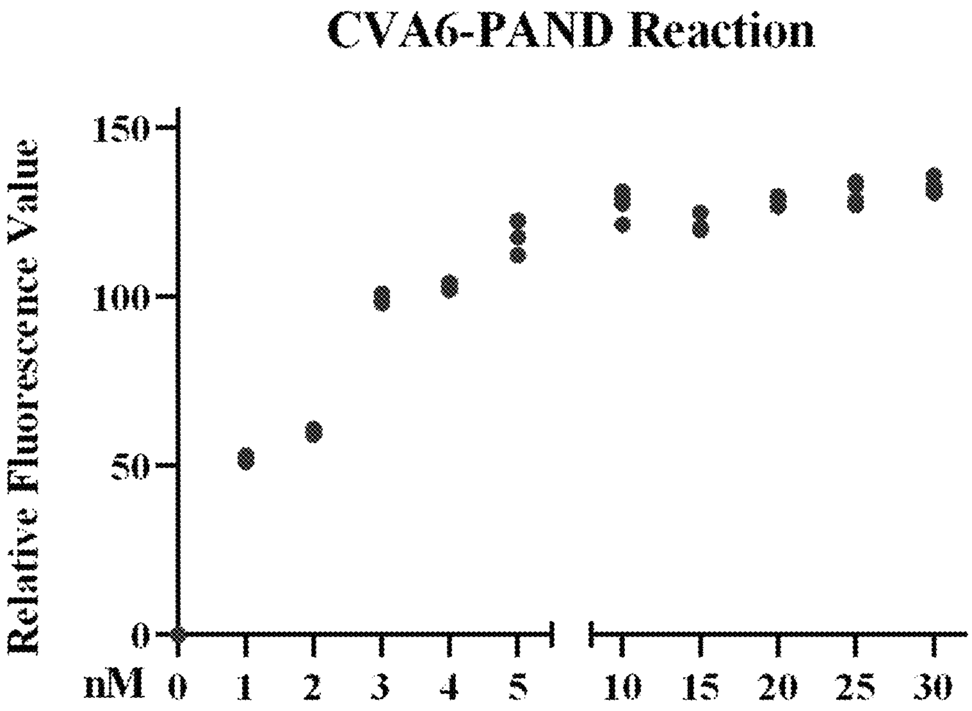
Figure 9D:
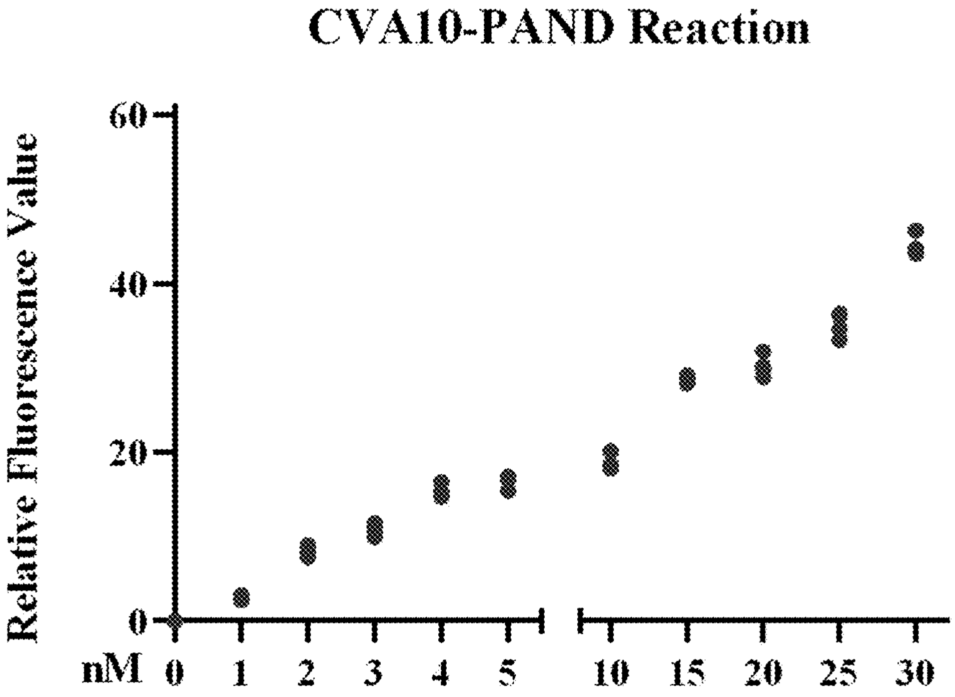
Figure 9E:
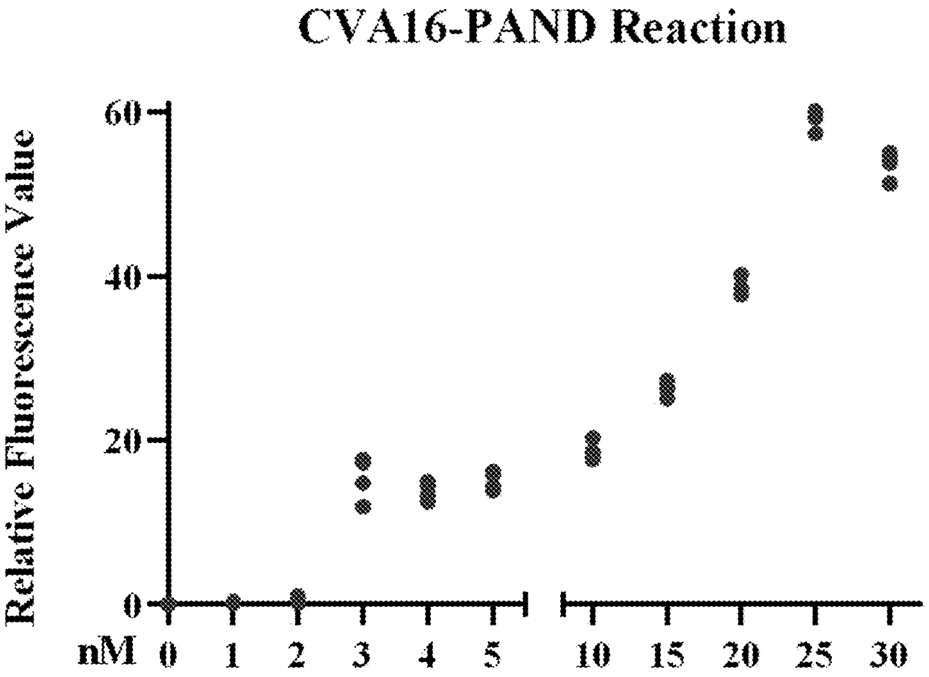
Figure 10A:
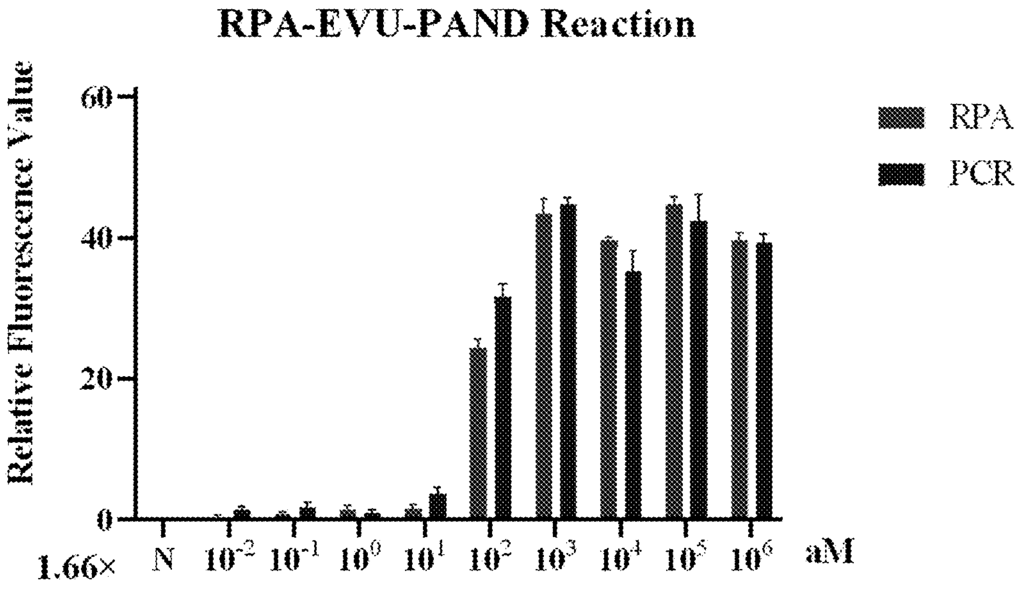
FIG. 10(*a*), FIG. 10(*b*), FIG. 10(*c*), FIG. 10(*d*) and FIG. 10(*e*) show sensitivity test results of an RPA-PAND method according to the present disclosure.
Figure 10B:
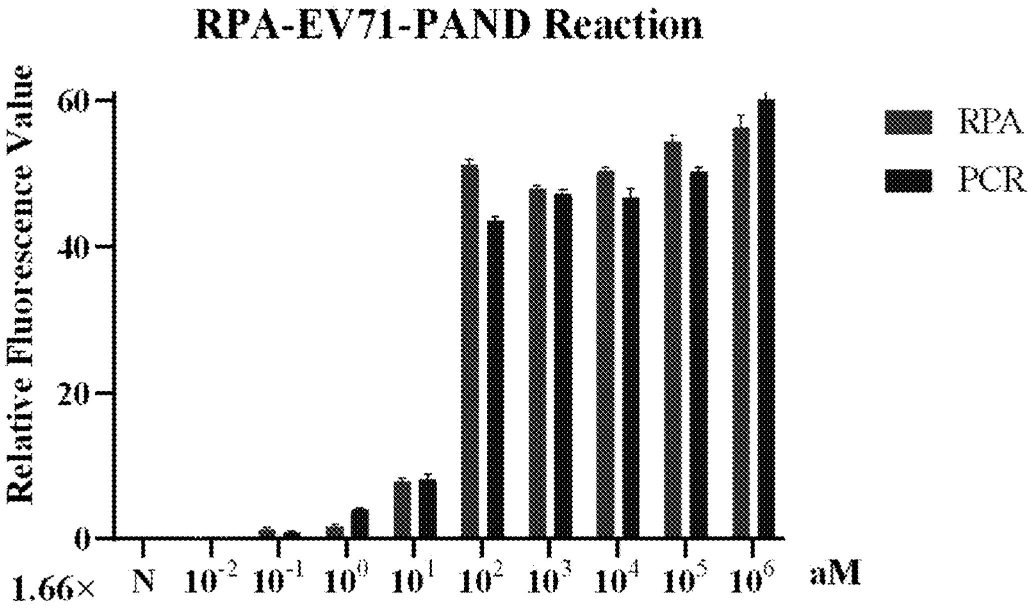
Figure 10C:
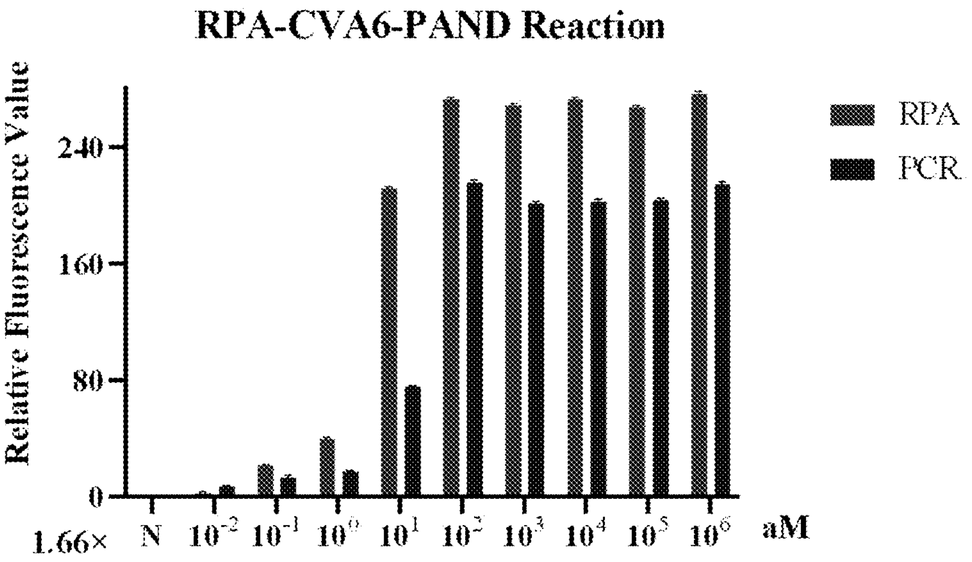
Figure 10D:
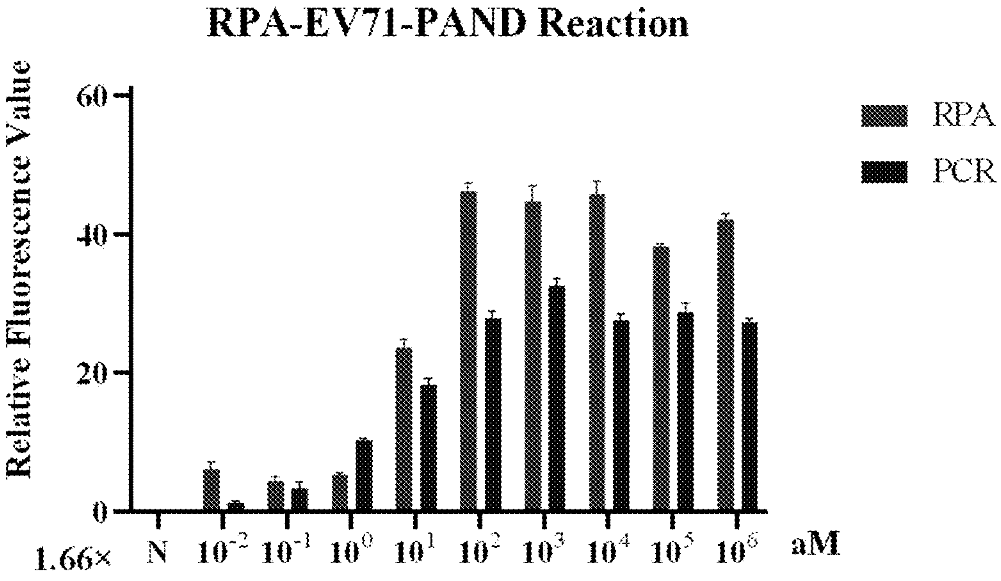
Figure 10E:
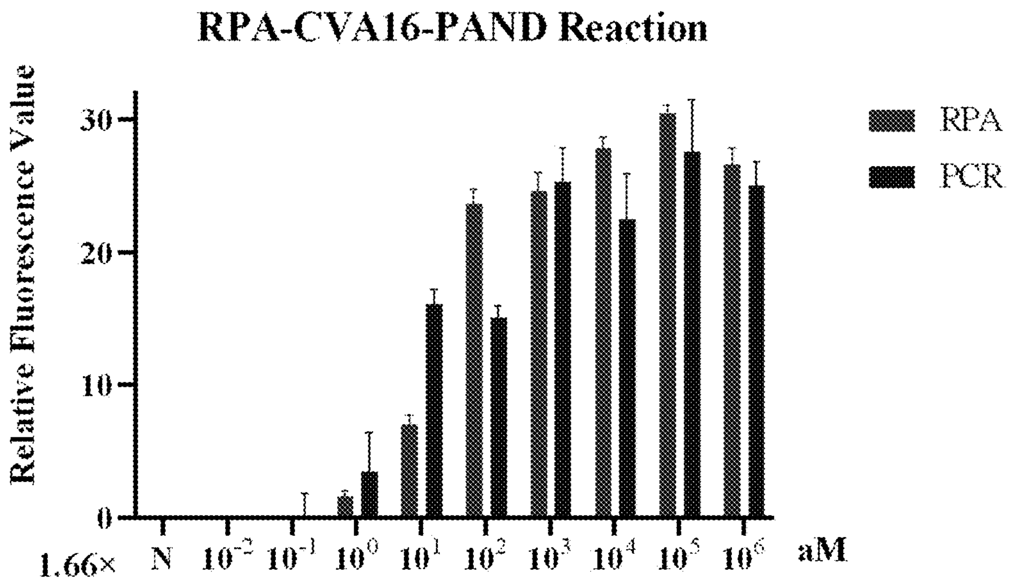

The RPA primers as shown in Table 4 were designed and screened through the following method: multiple RPA upstream and downstream primers were designed for a conversed fragment of each enterovirus according to a primer design principle required for RPA amplification reaction. For any enterovirus, an RPA amplification experiment was conducted utilizing different combined primers, which was specifically as follows: 29.4 μL of A buffer was added into each dry powder reaction tube, 2 μL of upstream/downstream primers (10 μM), a nucleic acid template and $ddH_2O$ were successively added after complete mixing, subsequently 2.5 μL of B buffer was added, and an amplification reaction was initiated after the above materials were sufficiently mixed (see Table 5); after incubation for 30 min at 37° C., an equal amount of amplification product was added into a 6×Loading buffer metal bath to be incubated for 5 min at 56° C. for 3% agarose gel detection. Finally, it was determined that there were still high-sensitivity amplification primer combinations under the low copy number. The agarose gel detection results of different enterovirus amplification products are as shown in FIG. 8.

TABLE 5

RPA amplification reaction system

| Component | Volume |
|---|---|
| DNA template | 5 μL |
| A buffer | 29.4 μL |
| B buffer | 2.5 μL |
| F (10 pmol/μL) | 2 μL |
| R (10 pmol/μL) | 2 μL |
| $ddH_2O$ | 9.1 μL |

The RPA amplification products of different combinations simultaneously underwent PAND detection (the same as example 1), then fluorescence signal intensity comparison was conducted by microplate reader detection, and finally the RPA primer pairs that are capable of producing relatively high fluorescence signal values in the enterovirus typing detection method using RPA combined with a PAND detection method were screened, specifically see Table 4.

Example 3

Based on the detection kit in example 2, an RPA-PAND method for detecting enterovirus typing was established in this example, specifically comprising the following steps:

(1) RPA Amplification

A to-be-detected sample was amplified by utilizing an RPA primer to obtain an RPA product, where the amplification conditions were preferably as follows: react for 10-20 min at 37° C.

(2) MB carrying a fluorophore (such as FAM) was synthesized, and a PAND detection system as shown in Table 7 was established for reaction, where the reaction conditions were preferably as follows: react for 30 min at 95° C.

TABLE 6

PfAgo-mediated PAND reaction system

| Component | Volume |
|---|---|
| His-PfAgo protein (10 pmol/μL) | 3 μL |
| Total gDNA (10 pmol/μL) | 3 μL |
| RPA product | 1 μL |
| PfAgo reaction buffer (10x) | 2 μL |
| $ddH_2O$ | 10.5 μL |
| MB (10 pmol/μL) | 0.5 μL |

After the reaction was ended, 20% TBE-PAGE electrophoresis was conducted, and staining was conducted for 5 min in the dark using SYBR Gold nucleic acid dye to verify digestion results.

In addition, in the step (2) of this method, the MBs of different enteroviruses carried different fluorophores in order to distinguish and identify various types of enteroviruses while simultaneously detecting changes in fluorescence signals.

Example 4

Based on example 3, the sensitivity test for a PAND method and an RPA-PAND method was conducted in this example. Compared with the RPA-PAND method, RPA amplification was replaced with the conventional PCR amplification reaction in the PAND method.

(1) Minimum Detectable Concentration (MDC) of PAND Method

Positive plasmids (the same as example 1) of different enteroviruses were amplified respectively through PCR reaction. The amplification products were purified (purified using an Omega glue recovery kit, and the purified products were measured using a NanoDrop 8000 high-throughput spectrophotometer) and then subjected to gradient dilution into 1, 2, 3, 4, 5, 10, 15, 20, 25 and 30 nM, and equal amounts of purified products were added in to a PAND detection system to react for 30 min at 95° C. The fluorescence values were measured according to a microplate reader to analyze the MDC.

The results are as shown in FIG. 9(*a*), FIG. 9(*b*), FIG. 9(*c*), FIG. 9(*d*) and FIG. 9(*e*). The lowest sensitivity of EVU can reach 1 nM, the lowest sensitivity of EV71 can reach 1 nM, the lowest sensitivity of CVA6 can reach 1 nM, the lowest sensitivity of CVA10 can reach 1 nM, and the lowest sensitivity of CVA16 can reach 3 nM.

(2) MDC of RPA-PAND Method

Based on a plasmid containing different enterovirus gene fragments as a target, the concentration of the plasmid was measured using NanoDrop 8000. According to the equation (copy number (copies/μL)=[$6.02\times10^{23}$×plasmid concentration (ng/μL)]/[DNA length (bp)×$660\times10^{9}$]), the copy number was calculated and diluted by 10 folds, with specific dilutions of $1.66\times10^{-2}$, $10^{-1}$, $10^{0}$, $10^{1}$, $10^{2}$, $10^{1}$, $10^{4}$, $10^{5}$ and $10^{6}$ aM. The RPA amplification was respectively conducted using RPA primers (react for 10 min at 37° C.). Equal amounts of amplification products were added into the PAND detection system to react for 30 min at 95° C., so as to determine the MDC of different typings.

The results are as shown in FIG. 10(*a*), FIG. 10(*b*), FIG. 10(*c*), FIG. 10(*d*) and FIG. 10(*e*). After combined with RPA or PCR amplification, the MDC levels of the 5 enteroviruses were significantly improved, respectively, which reached $1.66\times10^{-2}$–1.66 aM (0.01-1 copy/μL), where the MDC level of CVA16 was 1.66 aM, the MDC level of EV71 was $1.66\times10^{-1}$ aM, and the MDC levels of CVA6/10 and EVU reached $1.66\times10^{-2}$ aM. However, relative to combination with PCR amplification, the time required for RPA-HFMD-PAND detection was reduced by 45 min.

Meanwhile, qPCR detection was conducted using an equal amount of diluted plasmid template (see Table 7 and Table 8). The detection results show that the MDC level of RPA-HFMD-PAND is comparable to or even more sensitive than 10 times that of the qPCR method. The qPCR detection (the used primer sequence is the same as that of the RPA primer) results show that except that the qPCR detection lower limit of EV71 is 10 copy/μL (i.e., 16.6 aM), and the qPCR detection lower limits of the rest EVU, CVA6-VP1, CVA10-VP1 and CVA16-VP1 are 1 copy/μL (i.e., 16.6 aM). It is proved that the RPA-PAND detection method has the advantage of relatively high sensitivity.

TABLE 7

Fluorescence quantitative PCR system

| Component | Volume |
|---|---|
| qPCR SYBR Green Master Mix | 10 μL |
| F (10 μM) | 0.4 μL |
| R (10 μM) | 0.4 μL |
| DNA | 1 μL |
| $ddH_2O$ | 8.2 μL |

TABLE 8

Fluorescent quantitative PCR procedure

| Step | Time |
|---|---|
| Pre-denaturation at 95° C. | 5 min |
| Denaturation at 95° C. | 10 s |
| Annealing/extension at 60° C. | 30 s |
| Cycle number | 40 cycle |
| 65° C. | 5 s |
| 95° C. | 0.5° C. |

Example 5

Figure 11:
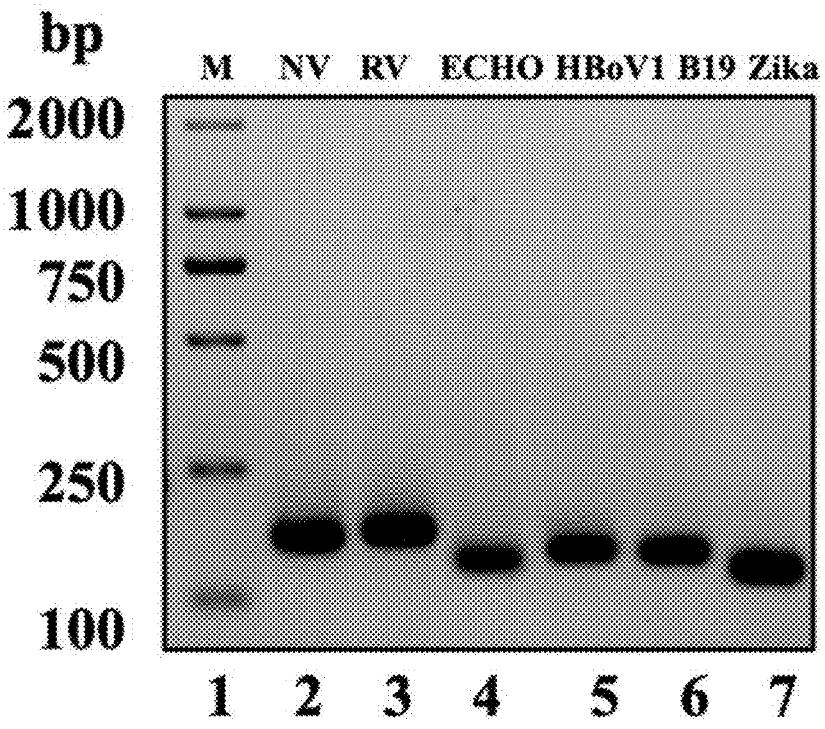
FIG. 11 shows agarose gel detection results of a non-enterovirus DNA fragment in example 5; M: DL2000 DNA maker; 1: Nodavirus VP1 region amplification fragment; 2: Rotavirus VP7 region amplification fragment; 3: Echovirus VP1 region amplification fragment; 4: Human Bocavirus I NP1 region amplification fragment; 5: Human Parvovirus B19 VP1 region amplification fragment; 6: Zika virus NS1 region amplification fragment.

The specificity test of the RPA-PAND detection method was conducted by using a conserved region gene fragment containing EVU, EV71, CVA6, CVA10 and CVA16 as a template and adding a non-enterovirus DNA fragment as a control experiment; the specificity of this method was verified by analyzing the fluorescence signal value change of a microplate reader amplification product. The specific processes are as follows:

(1) the conserved region gene fragments of EVU, EV71, CVA6, CVA10 and CVA16 and other non-enterovirus DNA fragments (including NV-VP1, RV-VP7, ECHO-VP1, HBoV1-NP1, B19-VP1 and Zika-NS1) were obtained through RPA amplification, and the agarose gel analysis results of the 6 DNA fragments are as shown in FIG. 11).

Figure 12:
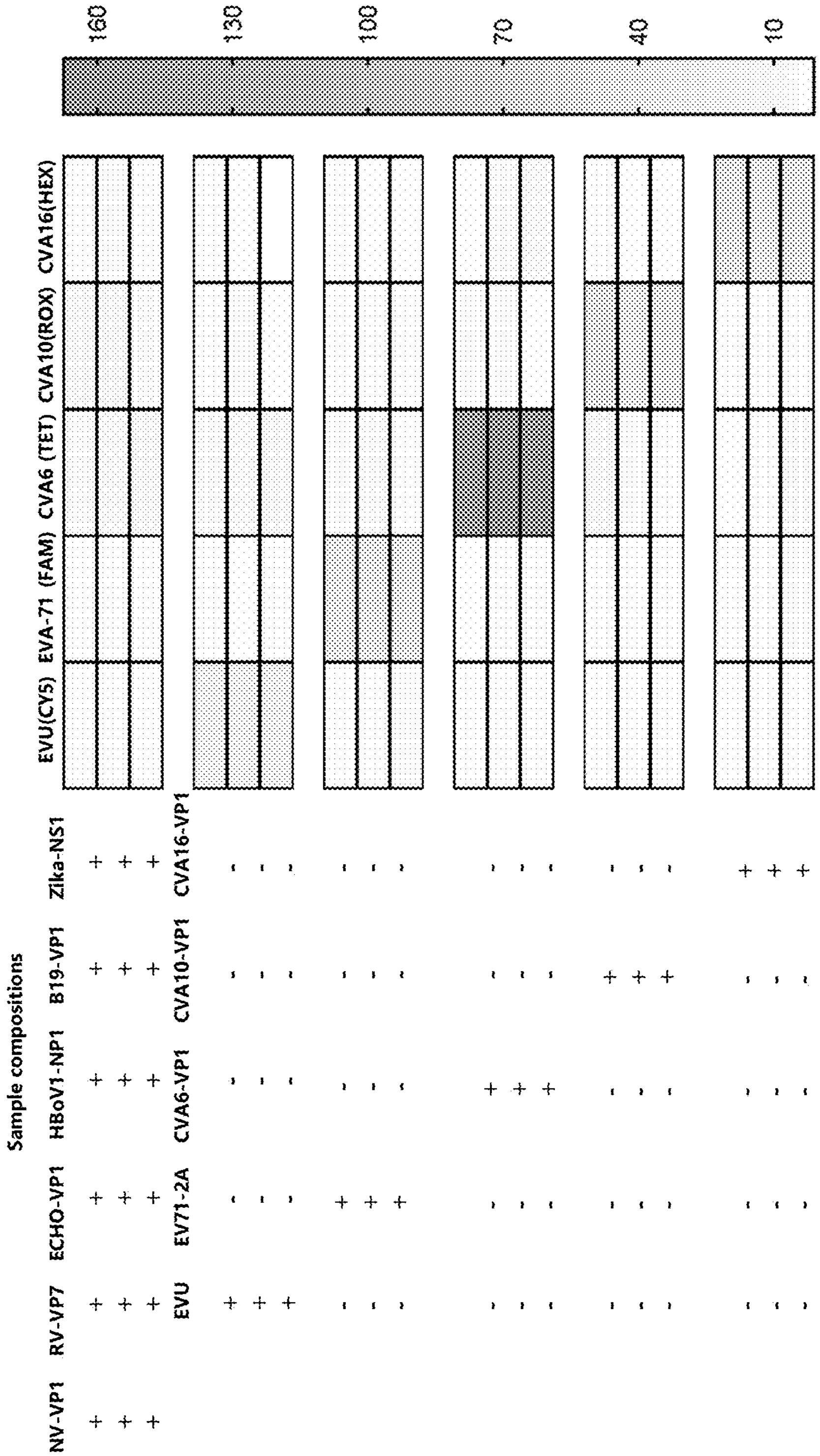
FIG. 12 shows specificity test results of an RPA-PAND method according to the present disclosure.

(2) By referring to Table 6, a PAND reaction system containing enteroviruses EVU, EV71, CVA6, CVA10, CVA16, and MB and gDNA was constructed; according to FIG. 12, different DNA fragments or combinations in step (1) were added into the PAND reaction system for reaction (react for 30 min at 95° C.).

The results are as shown in FIG. 12. Under the condition that the RPA amplification product that can be targeted by specific gDNA is only contained, the fluorescence signal in the reaction is enhanced, and there are no change difference values of fluorescence signals in non-enterovirus gene product reaction detection systems. It shows that the PfAgo-mediated PAND typing detection method for EVU, EV71-2A, CVA6-VP1, CVA10-VP1 and CVA16-VP1 is successfully established in the present disclosure, with relatively high specificity.

In conclusion, based on the PAND technology, the present disclosure focuses on the development of products (i.e., reagent kits) and methods (i.e., HFMD-PAND and RPA-HFMD-PAND) for enterovirus nucleic acid detection, and successfully used for typing detection of common enterovirus type A pathogens EV71, CVA6, CVA10, CVA16, and enterovirus universal EVU.

The main technical advantages of the present disclosure include: (1) compared with a detection platform based on a CRISPR-Cas system, the HFMD-PAND method can use low-cost guide DNA to screen a wider range of target regions, but not limited to PAM sequences; (2) relative to PCR amplification, the time required for RPA-HFMD-PAND detection is reduced by 45 min; (3) the MDC level of RPA-HFMD-PAND is comparable to, or even more sensitive than 10 times that of the qPCR method.

The performance indexes of the product and method of the present disclosure include: (1) the minimum detection concentration (MDC) of the HFMD-PAND method ranges from 1 nM to 3 nM on the premise that RPA amplification reaction is not combined; (2) after RPA or PCR amplification is combined, the MDC levels of the 5 enteroviruses are greatly improved respectively, which reach $1.66\times10^{-2}$–1.66 aM (0.01-1 copy/μL), wherein the MDC level of CVA16 is 1.66 aM, the MDC level of EVU71 is $1.66\times10^{-1}$ aM, the MDC levels of CVA6/10 and EVU are $1.66\times10^{-2}$ aM.

It is noted that the above embodiments are only some embodiments of the present disclosure but not all, and only for illustrating the technical solution of the present disclosure instead of limiting it. Based on the embodiments of the present disclosure, all the other embodiments obtained by those of ordinary skill in the art on the premise of not contributing creative efforts should belong to the scope of protection of the present disclosure.

What is claimed is:

1. An enterovirus typing detection kit, comprising:

A) a *Pyrococcus furiosus* Argonaute (PfAgo) protein;

B) five sets of guide DNA (gDNA) and molecular beacon (MB) combination, wherein each gDNA and MB combination is designed for detecting a specific enterovirus, selected from the group consist of EV71, CVA6, CVA10, CVA16 and universal enteroviruses (EVU), wherein each gDNA and MB combination comprises three gDNAs and one MB;

wherein, in the gDNA and MB combination for EVU detection:

the MB comprises the nucleotide sequence of SEQ ID NO: 2;

the three gDNAs each comprise one of nucleotide sequences of SEQ ID NO: 3 (EVU-g1), SEQ ID NO:4 (EVU-g2), and SEQ ID NO: 5 (EVU-g3);

in the gDNA and MB combination for EV71 detection:

the MB comprises the nucleotide sequence of SEQ ID NQ: 7;

the three gDNAs each comprise one of nucleotide sequences of SEQ ID NO: 8 (EV71-g1), SEQ ID NO: 9 (EV71-g2), and SEQ ID NO: 10 (EV71-g3);

in the gDNA and MB combination for CVA6 detection:

the MB comprises the nucleotide sequence of SEQ ID NO: 12;

the three gDNAs each comprise one of nucleotide sequences of SEQ ID NO: 13 (CVA6-g1), SEQ ID NO: 14 (CVA6-g2), and SEQ ID NO: 15 (CVA6-g3);

in the gDNA and MB combination for CVA10 detection:

the MB comprises the nucleotide sequence of SEQ ID NO: 17;

the three gDNAs each comprise one of nucleotide sequences of SEQ ID NO: 18 (CVA10-g1), SEQ ID NO: 19 (CVA10-g2), and SEQ ID NO: 20 (CVA10-g3);

in the gDNA and MB combination for CVA16 detection:

the MB comprises the nucleotide sequence of SEQ ID NO: 22;

the three gDNAs each comprise one of nucleotide sequences of SEQ ID NO: 23 (CVA 16-g1), SEQ ID NO: 24 (CVA16-g2), and SEQ ID NO: 25 (CVA 16-g3); and C) recombinase polymerase amplification (RPA) primer pairs consist of:

EVU-RPA-F (SEO ID NO: 26) and EVU-RPA-R (SEO ID NO: 27);

EV71-RPA-F (SEO ID NO: 28) and EV71-RPA-R (SEO ID NO: 29);

CVA6-RPA-F (SEO ID NO: 30) and CVA6-RPA-R (SEO ID NO: 31);

CVA10-RPA-F (SEO ID NO: 32) and CVAIO-RPA-R (SEO ID NO: 33);

CVA16-RPA-F (SEO ID NO: 34) and CVA16-RPA-R (SEO ID NO: 35).

2. The enterovirus typing detection kit according to claim 1, wherein the MB carries a fluorophore selected from the group consisting of FAM, CY5, TET, ROX and HEX.

3. The enterovirus typing detection kit according to claim 1, wherein the PfAgo protein comprises an amino acid sequence set forth in SEQ ID NO:36.

4. An enterovirus typing detection method, which is not intended to diagnose and treat diseases, and comprises the following steps:

S1, extracting DNA of a to-be-detected sample, amplifying with a RPA primer pair of the enterovirus typing detection kit according to claim 1 using the extracted DNA as a template to obtain an RPA product; wherein the RPA product comprises a target region for three guide DNAs (gDNA) and a molecular beacon (MB) corresponding to a specific enterovirus type;

S2, reacting with the PfAgo protein, the three gDNA and the MB in the enterovirus typing detection kit according to claim 1, by using the RPA product obtained in S1 as a detection object for reaction, wherein the MB carries a fluorophore selected from the group consisting of FAM, CY5, TET, ROX and HEX, and wherein different enterovirus types correspond to MBs carrying fluorophores with different detection wavelengths;

S3, measuring a fluorescence intensity of the MB in S2, and determining the type of enterovirus in the to-be-detected sample based on the detection wavelength of the fluorophore carried by said MB.

5. The enterovirus typing detection method according to claim 4, wherein, the condition for amplification by the RPA primer pair is as follows: react for 10-20 min at 37° C.

6. The enterovirus typing detection method according to claim 4, wherein the condition for reaction in the step S2 is as follows: react for 30 min at 95° C.

* * * * *